US005610192A

United States Patent [19]
Cohen et al.

[11] Patent Number: 5,610,192
[45] Date of Patent: Mar. 11, 1997

[54] INHIBITORS OF METAZOAN PARASITE PROTEASES

[75] Inventors: Fred E. Cohen; James H. McKerrow; Christine S. Ring, all of San Francisco; Philip J. Rosenthal, Nicasio; George L. Kenyon; Zhe Li, both of San Francisco, all of Calif.

[73] Assignee: The Regents of the University of California, Oakland, Calif.

[21] Appl. No.: 387,760

[22] PCT Filed: Sep. 13, 1993

[86] PCT No.: PCT/US93/08708

§ 371 Date: Mar. 28, 1995

§ 102(e) Date: Mar. 28, 1995

[87] PCT Pub. No.: WO94/06280

PCT Pub. Date: Mar. 31, 1994

Related U.S. Application Data

[63] Continuation-in-part of Ser. No. 943,925, Sep. 11, 1992, abandoned.

[51] Int. Cl.$^6$ .................................................. A61K 31/15
[52] U.S. Cl. .............................................. 514/614; 514/639
[58] Field of Search ........................................ 514/639, 614

[56] References Cited

PUBLICATIONS

Chen, et al., "Licochalone A, a New Antimalarial Agent, Inhibits In Vitro Growth of the Human Malaria Parasite *Plasmodium falciparum* and Protects Mice from *P. yoelii* infection", *Antimicrobial Agents and Chemotherapy*, 38(7):1470–1475 (1994).

Silfen, et al., "Bioflavonoid effects on in vitro cultures of *Plasmodium falciparum*. Inhibition of permeation pathways induced in the host cell membrane by intraerythrocytic parasite", *Chemical Abstracts*, 110(11):18, Col. 2, Abstract 87987p (1989).

Proceedings of the National Academy of Sciences, vol. 90, Issued Apr. 1993, Ring et al "Structural–Based Inhibitor Design by Using Protein Models for the Development of Antiparasitic Agents" pp. 3583–3587, See Entire Document Especially p. 3584 Figures.

Chemical Abstracts, vol. 115, No. 4, Issued 1991, Rheinberger et al. "Incorporation of Fluorescent Substances into Dental Materials for Differentiation from Surrounding Tissue," See Abstract No. 142380, Ger. Offen. DE 3939998.

Chemical Abstracts, vol. 81, No. 12, Issued 1974, Mucke, H., "Possibilities of Coloring Peracetic Acid for Skin Disinfection" See Abstract No. 68513, Pharmazie 29(3), 206–7.

Chemical Abstracts, vol. 113, No. 22, Issued 1989, Kino and Kato, "Hair Dyes Taining Water–Soluble Dyes, Carbon Black, and Nonionic Surfactants," See Abstract No. 197653, JP 01242518.

Sweeney et al. "Burger's Medicinal Chemistry" Fourth Edition, Part II. Published 1981 by John Wiley & Sons (N.Y.) pp. 342–345).

Santi et al. "Burger's Medicinal Chemistry" Fourth Edition, Part II. Published 1981 by John Wiley & Sons (N.Y.) pp. 350–351.

Rosenthal et al. The American Society for Clinical Investigation, Inc. "Antimalarial Effectis of Peptide Inhibitors of *Plasmodium Falciparum* Cysteine Proteinase" vol. 88, Nov. 1991, 1467–1472.

DoAmaral et al., J. Med. Chem. (12), pp. 21–25, Jan., 1969.

*Primary Examiner*—Phyllis G. Spivack
*Attorney, Agent, or Firm*—Robbins, Berliner & Carson, LLP

[57] ABSTRACT

Compositions and methods for treating a patient infected with a metazoan parasite by inhibiting the enzymatic action of the metazoan parasite protease. The compositions comprise at least one metazoan protease inhibitor which binds to the S2 subsite and at least one of the S1 and S1' subsites of the metazoan parasite protease. The methods comprise administration to a patient infected with a metazoan parasite of at least one metazoan protease inhibitor in an amount effective to inhibit the protease of the metazoan parasite, thereby killing the parasite.

18 Claims, 2 Drawing Sheets

INHIBITORS OF METAZOAN PARASITE PROTEASES

This invention was made with Government support under Contract No. MDA 972-91-J-1013, awarded by DARPA (Department of Defense); and Grant No. 890499 awarded by UNDP/World Bank/WHO Special Programme for Research and Training in Tropical Diseases (TDR). The Government has certain rights in this invention.

This patent application is based on PCT International Application PCT/US93/08708 filed on Sep. 13, 1993 (corresponding to PCT published application WO 94/06280, published on Mar. 31, 1994) which is a continuation-in-part of U.S. patent application Ser. No. 07/943,925 filed on Sep. 11, 1992, now abandoned.

BACKGROUND OF THE INVENTION

This invention relates generally to compositions and methods useful in the treatment of certain infectious diseases. More specifically, the invention relates to compositions which inhibit proteases, such as malaria cysteine protease. Compounds that inhibit these proteases are useful in the prevention and treatment of malaria, schistosomiasis and other infectious diseases.

Proteases are involved in many important biological processes including protein turnover, blood coagulation, complement activation, hormone processing, and cancer cell invasion. Thus, they are frequently chosen as targets for drug design and discovery. The critical role certain proteases play in the life cycle of parasitic organisms also makes them attractive drug design targets for certain infectious diseases.

Schistosomiasis (bilharziasis) is a parasitic disease caused by schistosomes (blood flukes) that generally live in the veins of the gut and liver of a human host. Adult worms can survive up to 20 years. Female adult worms release thousands of eggs each day, which often find their way to tissues such as liver, brain, and lung, where they cause considerable damage by stimulating the body to form inflammation and scar tissue around them. Most eggs pass through the bladder or wall of the gut. Once outside, they hatch and infect water snails. The parasite multiplies inside the snail, giving rise to thousands of cercariae that exit the snail and swim free in search of a host in which to complete their life cycle.

Malaria is another well known infectious disease caused by protozoa of the genus Plasmodium, which are transmitted by bites of infected mosquitoes. Infection with *Plasmodium falciparum*, the most virulent human malarial pathogen, is estimated to be responsible for over 1 million deaths each year. The most valuable of the heretofore developed classes of antimalarial drugs are the quinoline-containing compounds, such as chloroquine and mefloquine; chloroquine has been especially effective as both a preventative and a curative. A serious problem in the treatment and control of malaria has been the increasing resistance of populations of *P. falciparum* to these known antimalarial drugs. In addition, reports of multi-drug resistance makes the search for novel therapies especially urgent. Thus, there remains a great need to identify new compounds that have antimalarial capabilities.

During the trophozoite stage, the parasites infect red blood cells (erythrocytes) where they reproduce asexually. At the completion of each asexual cycle, the red blood cells lyse and merozoites are released which invade new red blood cells. This cycle of lysis and re-infection is responsible for the major clinical manifestations of malaria.

Most anti-malarials are blood schizontocides which are active against the parasites during the intra-erythrocytic stage of its life cycle. Sulphones and sulphonamides inhibit the synthesis of dihydrofolic acid, while biguanides and diaminopyrimidines inhibit the synthesis of tetrahydrofolic acid. Although the mechanism of these anti-malarials is known to involve interference with the parasites' ability to synthesize nucleic acids [Bruce-Chwatt, L. J., *Essential Malariology* (Wiley, New York (1985))], the mechanism of action of the quinoline-containing compounds has until recently been surprisingly elusive. Recent work provides strong evidence that the quinoline derivatives work by interfering with the detoxification activity of a heme polymerase [Slater and Cerami, *Nature* 355, 167 (1992)].

During the erythrocytic phase, the parasites degrade hemoglobin as a primary cysteine protease involved in the degradation of hemoglobin, the parasites' primary source of amino acids [Rosenthal, P. J. et al., *J. Clin. Invest.* 82, 1560 (1988)]. Blocking this enzyrme with cysteine protease inhibitors (such as E-64 and Z-Phe-Arg-FMK) in culture arrests further growth and development of the parasites [Rosenthal, P. J. et al., *Mol. Biochem. Parasitol.* 35, 177 (1989)]. Because humans (and, probably, most other mammals) do not have an analogous hemoglobinase, inhibition of this protease (either alone or in conjunction with established therapies) provides an attractive strategy for the treatment of malaria. Moreover, inhibition of analogous proteases present in other metazoan parasites would similarly provide potentially valuable techniques for treatment of human and animal patients infected with those parasites.

It is an object of the present invention to provide compositions and methods for treatment of malaria.

It is a further object of the present invention to provide compositions and methods useful in the treatment of other infectious diseases caused by metazoan parasites.

SUMMARY OF THE INVENTION

In accordance with the present invention, there are provided compositions and methods for treating a patient infected with a metazoan parasite by inhibiting the enzymatic action of the metazoan parasite protease. These compositions and methods have particular utility in the treatment of schistosomiasis, malaria, and other infectious diseases. The compositions comprise at least one metazoan protease inhibitor (as hereinafter defined) containing specific structural elements which bind to the S2 subsite and at least one of the S1 and S1' subsites of the metazoan parasite protease. The protease inhibitors of the present invention generally include at least two homoaromatic or heteroaromatic ring systems, each comprising one to three rings, joined together by suitable linkers. The compositions of the present invention are useful, for example, to inhibit the action of trophozoite cysteine protease, thereby preventing degradation of hemoglobin, the primary source of amino acids for the pathogen that causes human malaria. The methods of the present invention comprise administration to a patient infected with a metazoan parasite of at least one metazoan protease inhibitor in an amount effective to inhibit the protease of the metazoan parasite, thereby killing the parasite.

BRIEF DESCRIPTION OF THE DRAWINGS

The invention may be better understood with reference to the accompanying drawings, in which.

DETAILED DESCRIPTION OF THE INVENTION

Pursuant to the present invention, compositions and methods for inhibiting the enzymatic action of metazoan parasite proteases comprising an effective amount of at least one metazoan protease inhibitor (as hereinafter defined) are provided. These compositions have utility in the prevention and treatment of schistosomiasis, malaria, and other infectious diseases. In the case of malaria, the compositions of the invention inhibit the trophozoite cysteine protease. In schistosomiasis, the enzyme inhibited by the compositions of the invention is the adult cysteine protease (or "hemoglobinase").

The inhibitors of the present invention have particular utility against the metazoan parasites *Plasmodium falciparum* (which causes malaria), *Schistosoma mansoni* (which causes schistosomiasis), and *Trypanosoma cruzi* (which causes chagas' disease). In addition, proteases specific to the following metazoan parasites may also be inhibited by compositions in accordance with the present invention: *Giardia lamblia, Entoemeba histolytica, Cryptospiridium spp., Leishmania spp., Brugia spp., Wuchereria spp., Onchocerca spp., Strongyloides spp., Coccidia, Haemanchus spp., Ostertagia spp., Trichomonas spp., Dirofilaria spp., Toxocara spp., Naegleria spp., Pneumocystis carinii, Ascaris spp.,* other *Trypanosoma spp.,* other *Schistosome spp.,* other *Plasmodium spp., Babesia spp., Theileria spp., Anisakis* and *Isospora beli*.

The structure for a model metazoan protease, malaria cysteine protease, was developed using sequence information and the x-ray structures of papain and actinidin as a basis for homology modeling following the approach of Sutcliffe and co-workers [Sutcliffe. M. J. et al., *Protein Engineering* 1, 377 (1987); Sutcliffe, M. J. et al., *Protein Engineering* 1, 385 (1987)]. The protease model structure was used as target receptor in a search for potential ligands. DOCK3.0 is an automatic method to screen small molecule databases for possible ligands of a given receptor [Meng, E. C. et al., *J. Comp. Chem.* 13, 505 (1992)]. DOCK3.0 was used to search the Fine Chemicals Directory of approximately 56,000 commercially available small molecules. The 2200 molecules with the best shape complementarity scores and the 2200 with the best force field scores (estimated interaction energies) were saved. The resulting 4400 compounds were visually screened in the context of the active site using the molecular display software MidasPlus [Ferrin, T. et al., *J. Mol. Graphics* 6, 13 (1988)]. An effort was made to choose a diverse group of compounds from these lists. Thirty-one compounds were ultimately chosen for initial testing on the malaria cysteine protease, and from these compounds a number of potential inhibitors were identified from experimental tests against the enzyme system. This constituted the first successful attempt to use computer-assisted docking of non-peptidic molecules to a model of an enzyme's three-dimensional structure.

Figure 1:
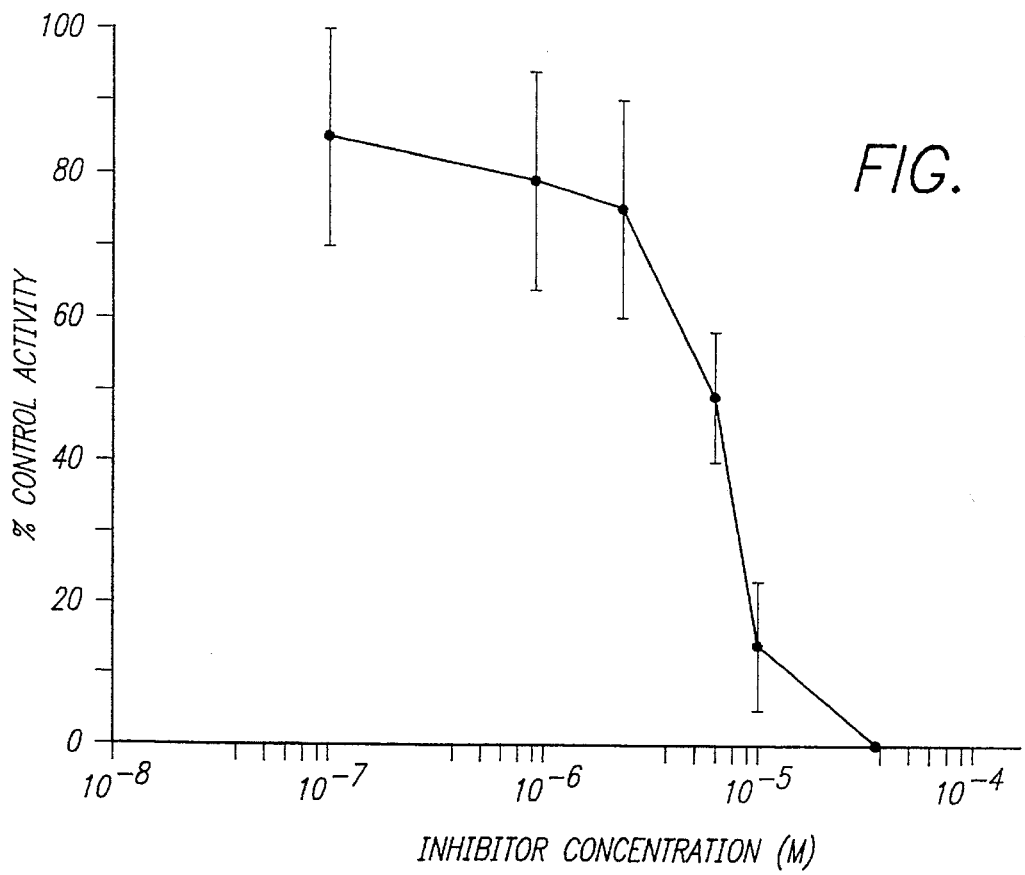
FIG. 1 is the $IC_{50}$ curve for oxalic bis-[(2-hydroxyl-1-naphthylmethylene)-hydrazide] against the malarial cysteine protease.
Figure 2:
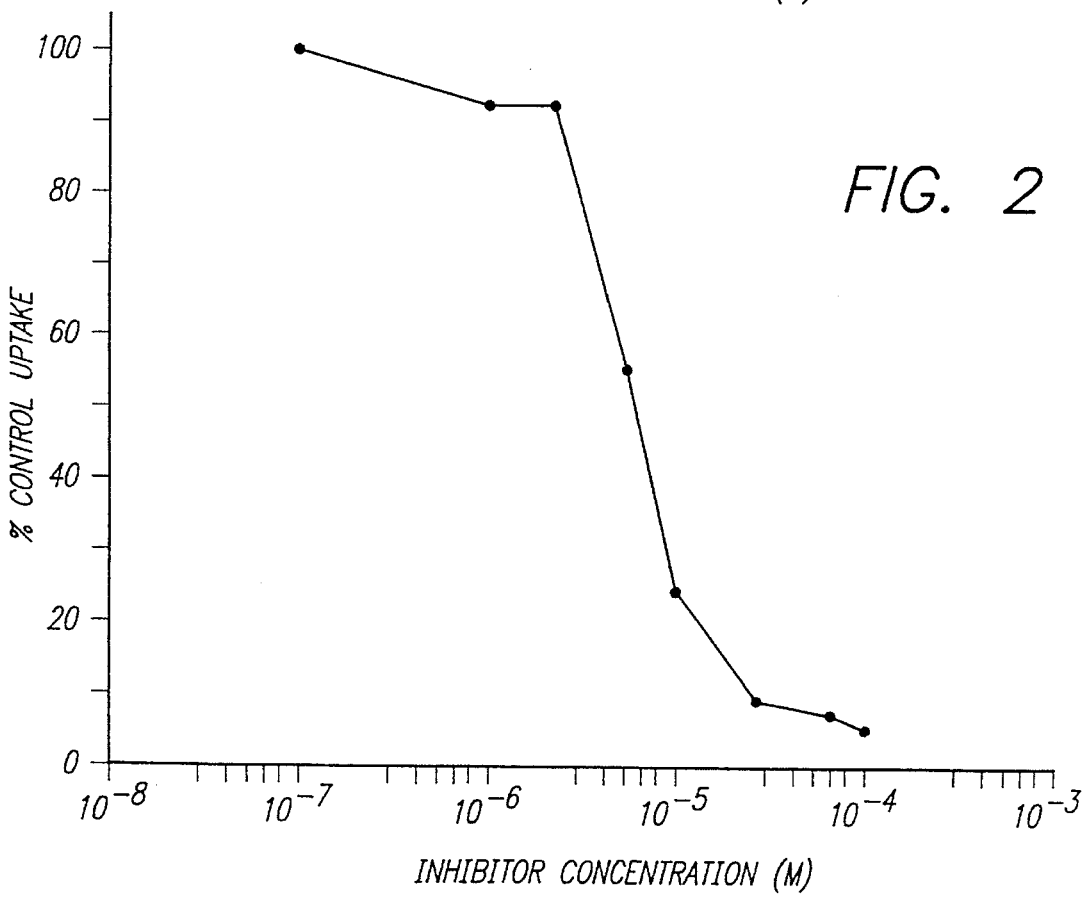
FIG. 2 illustrates the inhibition of the parasite uptake of $^3$H-hypoxanthine by oxalic bis-[(2-hydroxyl-1-naphthylmethylene)hydrazide]

Of the compounds originally considered as potentially useful inhibitors, oxalic bis-[(2-hydroxyl-1-naphthylmethylene)-hydrazide] and N,N-bis(2-hydroxy-1-naphthylmethylene)hydrazone were identified as the best inhibitors of the protease. The $IC_{50}$ of N,N-bis(2-hydroxy-1-naphthylmethylene)hydrazone for enzyme inhibition against the substrate Z-Phe-Arg-AMC was 5 μM. The $IC_{50}$ of oxalic bis[(2-hydroxy-1-naphthylmethylene) hydrazide] in the same assay was 6 μM (FIG. 1); more importantly, the compound kills parasites in culture at approximately the same concentration as judged by hypoxanthine uptake, a standard measure of *Plasmodium* viability (FIG. 2). Oxalic bis[(2-hydroxy-1-naphthylmethylene)hydrazide] was selected as the basis for further structure/activity studies and was designated as compound 143A.

It had previously been demonstrated that papain-like cysteine proteases contain active sites that could accommodate up to seven amino acids [Berger & Schechter, *Phil. Trans. Roy Soc. Ser.* B 257, 249 (1970)]. In the literature nomenclature, the active sites are numbered consecutively starting from the catalytic site S1 to Sn towards the amino terminus and S1' to Sn'0 towards the carboxyl terminus. The S2, S1 and S1' subsites are believed to be the most important for binding.

Figure 3:
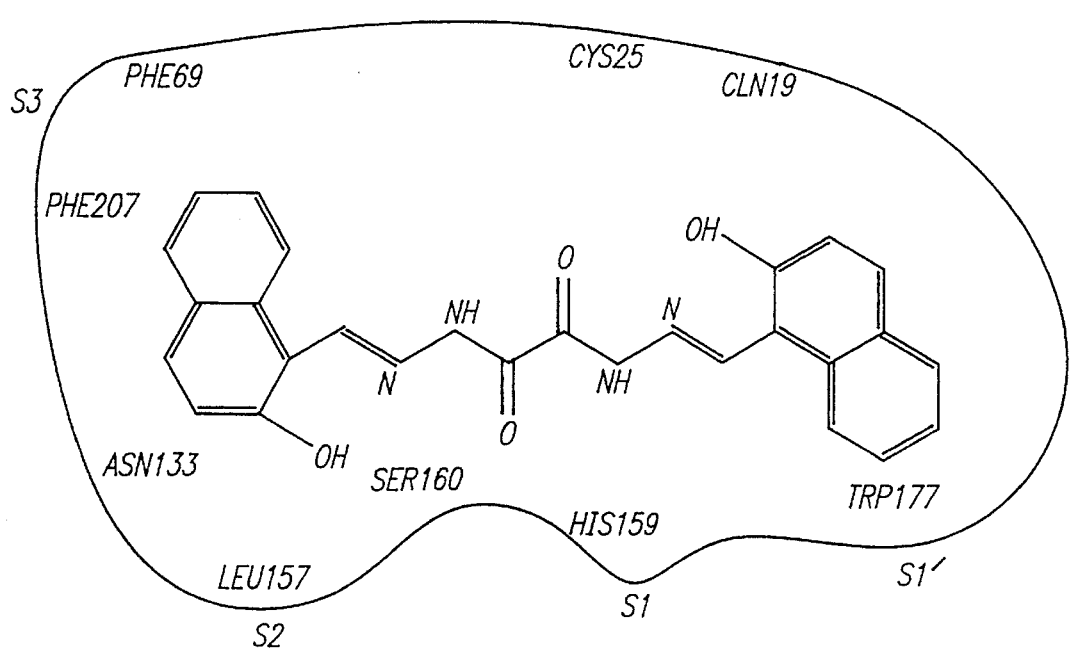
FIG. 3 is a schematic of oxalic bis-[(2-hydroxy-1-naphthylmethylene)-hydrazide] docked into the active site of trophozoite cysteine protease.

Because oxalic bis-[(2-hydroxyl-1-naphthylmethylene)-hydrazide] is a rigid and symmetric molecule, there are essentially two ways to orient the compound in the active site. In both, the compound lays across the active site cleft of malaria cysteine protease with one naphthol group fitting into the S2 specificity pocket and the other stacking with the indole ring of tryptophan 177 in the S1' pocket. The presumed binding mode is shown in FIG. 3. This orientation was chosen for illustration, as it maximizes the compound's interaction with the enzyme, each hydroxyl being within hydrogen bonding distance to a suitable residue in the enzyme (Ser160 and Gln19, respectively). Alternatively, the compound could be rotated 180° through the horizontal axis; although the hydroxyls do not interact with the enzyme, they presumably interact with solvent water molecules.

The original ligand coordinates of oxalic bis-[(2-hydroxyl-1-naphthylmethylene)hydrazide] supplied by DOCK3.0 were optimized by rotation and translation of the ligands without internal changes in ligand bond length, bond angle or torsional angles subject to the constraints of a semi-empirical molecular force field to provide a rigid body minimized complex for the molecule. Starting with the rigid body minimized complex of oxalic bis-[(2-hydroxyl-1-naphthylmethylene)-hydrazide], the volume limits of the S2 and S1' subsites were then explored by varying the size, composition and substituent patterns on the aromatic ring systems determined to be effective in binding to the target subsites of the protease model. Simultaneously, the linker length was varied to find the optimum spacing between the ring systems. In this manner, optimal ring systems and spacer lengths have been determined in accordance with the present invention for protease inhibitors which bind to the S2 and S1' subsites.

In addition, it has further been determined in accordance with the present invention that compounds comprising aromatic ring systems characteristic of the inhibitors useful for binding to the S2 and S1' subsites but joined by shorter linkers than would be appropriate for bridging these subsites were also effective in inhibiting metazoan parasite proteases.

Modeling studies with these shorter compounds indicates that one of the aromatic ring systems binds to the S2 subsite, as is the case with the inhibitors based on oxalic bis-[(2-hydroxyl-1-naphthylmethylene)-hydrazide]. However, instead of interacting with the S1' subsite, the second aromatic ring system of the shorter compounds binds to the S1 subsite. These shorter compounds are of particular interest as they can be synthesized in a one-step condensation of the corresponding aldehyde and hydrazine. Moreover, by introduction of a third aromatic ring system into the shorter inhibitors it is possible to construct compounds that fit all three pockets of the target site of the enzyme (the S2, S1 and S1' subsites).

On the basis of these structure/activity studies, a broad class of metazoan parasite protease inhibitors have been identified as of particular utility in accordance with the present invention having the general structure

A-X-B wherein A is a substituted or unsubstituted homoaromatic or heteroaromatic ring system comprising one to three rings which binds to the S2 subsite;

B is a substituted or unsubstituted homoaromatic or heteroaromatic ring system comprising one to three rings which binds to the S1 or S1' subsite; and X is a linker comprising a substantially planar linear array with a backbone of four to eight atoms in length.

In a first preferred class of inhibitors in accordance with the present invention, B binds to the S1' subsite and X is a linker with a backbone of six to eight atoms in length. In a second preferred class of inhibitors in accordance with the present invention, B binds to the S1 subsite and X is a linker with a backbone of about 4 atoms in length. In a preferred subclass of this second preferred class, B has the structure— B'-X'-B", wherein B' is an aromatic ring system which binds to the S1 subsite, B" is an aromatic ring system which binds to the S1' subsite, and X' is a direct bond or a linker with a backbone of one to three atoms in length.

The ring system A is preferably a one- or two-ring homoaromatic (e.g., phenyl, 1-naphthyl, 2-naphthyl, etc.) or heteroaromatic group which has an affinity for the S2 subsite of the metazoan parasite protease. The ring system A may be unsubstituted; preferably, however, the ring system A bears at least one non-interfering substituent (as hereinafter defined) which does not interfere with, and may actually promote, the binding in the S2 subsite via interactions with the side chains with hydrophobic features, side chains and polypeptide backbone elements with donor and acceptor sites for hydrogen bonds and side chains with formal charges for electrostatic interactions characteristic of the S2 subsite. A particularly preferred class of ring systems A are those that are substituted by one or more hydroxyl groups, as hydroxyl is believed to be especially effective in promoting binding to the subsite; groups with up to three hydroxyl substituents have shown good affinity for the S2 subsite.

Particular examples of suitable A systems include, but are not limited to, the following: phenyl; 1-naphthyl; 1-isoquinolyl; 1-phthalazinyl; 3-coumarinyl; 9-phenanthryl; and 1-quinolyl. Again, all of these ring systems may be unsubstituted or substituted by one or more non-interfering substituents as hereinafter defined. Among the phenyl systems, particular embodiments of interest include, but are not limited to, the following: 1-hydroxyphenyl; 2,3-dihydroxyphenyl; 1,2,3-trihydroxyphenyl; and 3-di-(lower-alkyl)-aminophenyl. Particularly preferred as ring system A is 1-naphthyl:

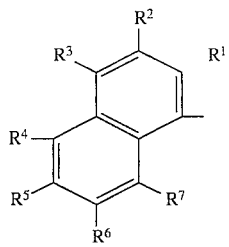

In addition to the unsubstituted 1-naphthyl group, the following substituted 1-naphthyl systems have been found especially useful in inhibitors within the scope of the present invention: $R^1$=OH; $R^3$=OH; $R^1$=lower alkoxy (e.g., —OCH$_3$); $R^3$=lower alkoxy (e.g., —OCH$_3$); $R^3$=lower alkyl (e.g., —CH$_3$); $R^3$=di-(lower-alkyl)-amino (e.g., —N(CH$_3$)$_2$; $R^4$=NO$_2$; $R^7$=COOH; $R^1$, $R^3$=OH; $R^1$, $R^2$=OH; $R^2$, $R^7$=OH; $R^1$, $R^5$=OH; $R^3$, $R^6$=OH; $R^1$, $R^7$=OH; $R^3$, $R^5$=OH; $R^1$, $R^4$=OH; $R^1$, $R^6$=OH; $R^1$=OH, $R^5$=NO$_2$; and $R^1$=OH, $R^5$=Br.

The choice of a particular structure for use as ring system B depends to some extent on whether the inhibitor is being designed for use to block the S1' subsite (i.e., an inhibitor comprising a longer linker) or the S1 subsite (i.e., an inhibitor comprising a shorter linker). In general, it has been determined that for binding to the S1' subsite, a two-ring system (for example, as described for use as Group A) is more effective than a one-ring system. In addition, ring systems bearing a substituent containing a heteroatom (O, N) and/or heterocyclic systems with charged atoms (in particular, quinoline) are preferred. On the other hand, the one- and two-ring systems are essentially equally effective for use in binding to the S1 subsite.

For use in binding to the S1 subsite, the following multiple-ring systems are preferred, each of which again may be unsubstituted or substituted by one or more non-interfering substituents (as hereinafter defined): 1-naphthyl; 2-naphthyl; 2-quinolyl; 3-quinolyl; 6-coumarinyl; 2-chromonyl (4-oxo-1,4-chromen-2-yl). Particularly preferred are a number of substituted 2-naphthyl systems, including but not limited to the following: 3-hydroxy-2-naphthyl; 3-(lower-alkoxy)-2-naphthyl; 5-hydroxy-2-naphthyl; and 4,7-dibromo-2-naphthyl. In addition, phenyl and substituted phenyl groups are also useful in binding to the S1 subsite. The multiple-ring systems (and in particular, two-ring systems) previously described as useful in binding to the S2 and S1 subsites are also presently preferred for binding to the S1' subsite.

The choice of linker X, as previously indicated, is dependent upon the particular subsites to which the particular inhibitor is targeted. For inhibitors directed to the S2 and S1' subsites, linkers containing a backbone consisting of six-eight atoms are particularly preferred; for inhibitors directed to the S2 and S1 subsites, however, linkers containing a backbone consisting of four atoms are especially useful. In all cases, the backbone may comprise one or more heteroatoms (N, O, S, etc.) in addition to carbon. Moreover, particularly suitable linkers have a relatively planar character induced by multiple bonds either in the backbone (e.g., —C=C—, —C=N—, etc.) or external thereto (e.g., —C(=O)—, —C(=S)—, etc.). Most preferred are linkers wherein there is an extended, substantially conjugated system of multiple bonds and heteroatoms with unshared electron pairs (e.g., O, N, S, etc.) which tends to maintain a relatively planar arrangement. However, linkers in which the backbone includes an alicyclic group (e.g., 1,3- or 1,4-cyclohexyl) are also contemplated as within the scope of the present invention. These linkers may also be substituted with one or more non-interfering groups (as hereinafter defined).

Examples of suitable linkers wherein the backbone consists of four atoms include the following (the atoms constituting the linker backbone being indicated in bold face):

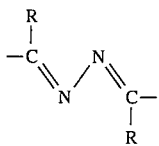

wherein R is hydrogen or lower alkyl;

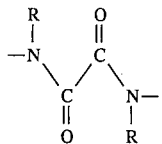

wherein R is hydrogen or lower alkyl;

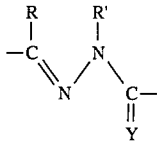

wherein R is hydrogen or lower alkyl, R' is hydrogen or lower alkyl, and Y is O or S; and

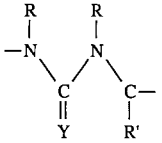

wherein R is hydrogen or lower alkyl, R' is hydrogen or lower alkyl, and Y is O or S. The first of the listed structures is particularly preferred, in view of the ease of synthesis of compounds containing this structure by reaction of the appropriate aldehyde and hydrazide.

For use in inhibitors targeted to the S2 and S1' subsites, linkers wherein the backbone contains 6 to 8 atoms are particularly suitable. Structures of interest include the following:

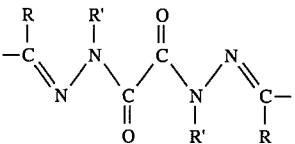

wherein R is hydrogen or lower alkyl and R' is hydrogen or lower alkyl;

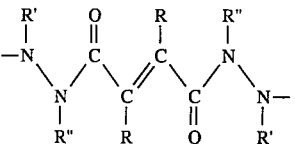

wherein R, R' and R" are independently selected from hydrogen and lower alkyl;

or

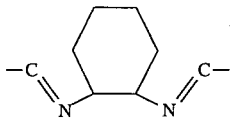

wherein the cyclohexyl group is unsubstituted or substituted by one or more non-interfering substituents (as hereinafter defined); and

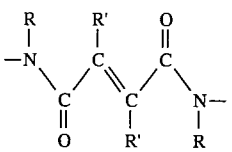

wherein R and R' are independently selected from hydrogen and lower alkyl. Of course, other structures containing backbones having the requisite number of atoms and exhibiting substantial planar character would be immediately apparent to those skilled in the art and are contemplated as suitable for use in accordance with the present invention.

As previously noted, both the ring systems A and B and the linker X may suitably bear one or more non-interfering substituents. For purposes of the present invention, a non-interfering substituent is defined as one which does not interfere with bonding of the ring structures to the active site of the enzyme due to steric and/or electronic factors; in some cases, the presence of particular non-interfering substituents is believed to promote bonding by interaction of these substituents with structural elements of the enzyme in the proximity of the active site. In most instances, the primary consideration with respect to possible substituents is a steric one; for the most part, relatively bulky substituents are not particularly preferred for use in the inhibitors of the present invention. Suitable non-interfering substituents include, but are not limited to, the following: hydroxyl, including protected hydroxyl (i.e., a hydroxyl group which is protected by a suitable art-recognized protective group); lower alkyl; lower alkoxy; amino, mono- and di-(lower-alkyl)-amino; —COOH and —COOR', wherein R' is lower alkyl or aryl; —NO$_2$; halogen (in particular, Cl, F and Br); aryl (in particular, phenyl and benzyl); and aryloxy (in particular, phenoxy and benzyloxy). For purposes of the present invention, by lower alkyl is meant an alkyl group of one to five, and preferably one to three, carbon atoms.

Particular inhibitors suitable for use in the compositions and methods of the present invention include a number of general classes of compounds which have been investigated in some detail. One such class of compounds wherein X has a backbone of four atoms has the general formula:

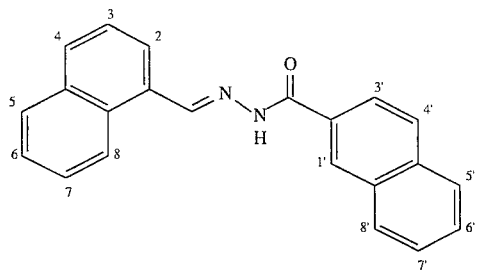

wherein the substitution pattern is advantageously selected from those reported in Table 1.

TABLE 1

| COMPOUND | SUBSTITUENTS |
|---|---|
| I193A | 2-OH, 3'-OH |
| III23A | 2-OH, 6-NO$_2$, 3'-OH |
| III41A | 2,3-OH, 3'-OH |
| III43A | 2,4-OH, 3'-OH |
| III45A | 2,7-OH, 3'-OH |
| III53A | 2-OMe, 3'-OMe, NMe |
| III55A | 2-OMe, 3'-OH |
| III59A | 4,8-OH, 3'-OH |
| III71A | 4-F, 3'-OH |
| III79A | 2,6-OH, 3'-OH |
| III81A | 4,7-OH, 3'-OH |
| III91A | 5-NO$_2$, 3'-OH |
| III93A | 2-H, 3'-OH |
| III95A | 4-Me, 3'-OH |
| III97A | 4-OH, 3'-OH |
| III115A | 4-NMe$_2$, 3'-OH |
| III128A | 2-OH, 3'-H |
| III130A | 2-OMe, 2'-OMe |
| III127A | 2-OH, 1'-OH |
| III132A | 8-COOH, 3'-OH |
| III133A | 2-OH, 3'-OH, 7'-OMe |
| III134A | 2-OH, 3',5'-OH |
| III135A | 2-OH, 1',4'-OH, OMe |
| III138A | 4-OMe, 3'-OH |
| III144A | 2,8-OH, 3'-OH |
| III145A | 4,6-OH, 3'-OH |
| III146A | 2,5-OH, 3'-OH |
| III151A | 2-OH, 6'-OH |
| III152A | 2-OH, 1'-Me |
| III153A | 2-OH, 8'-Ph |
| III154A | 2-OH, 3'-Br |
| III155A | 2-OH, 3'-NHMe |
| IV17A | 2-OH, 3'-OH, 4'-N$_2$(2-Cl, 5-CF$_3$-Phe) |

Another class of compounds wherein X also has a backbone of four atoms having particular utility as inhibitors of metazoan parasite proteases have the general formula

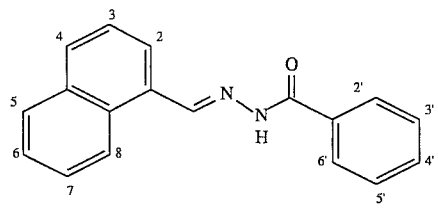

wherein the substitution pattern is advantageously selected from those reported in Table 2.

TABLE 2

| Compound | Substituents |
|---|---|
| III85A | 2-OH, 4'-Ph |
| III87A | 2-OH, 3'-OPh |
| III103A | 2-OH, 2'-OPh |
| III109A | 2-OH, 2'-OH |
| IV36A | 2,4-OH, 2'-OH |
| IV37A | 2,7-OH, 2'-OH |
| IV38A | 2,6-OH, 2'-OH |
| IV39A | 2-OH, 6-NO$_2$, 2'-OH |
| IV44A | 2-OH, 2',4'-OH |
| IV45A | 2-OH, 3',4'-OH |
| IV46A | 2-OH, 2'-H |
| IV47A | 2-OH, 3',5'-OH |
| IV49A | 2-OH, 2'-OMe |
| IV50A | 2-OH, 2'-F |
| IV51A | 2-OH, 3',4'-NH$_2$ |

Yet another class of compounds wherein X has a backbone of four atoms having particular utility as inhibitors for use in accordance with the present invention have the general formula

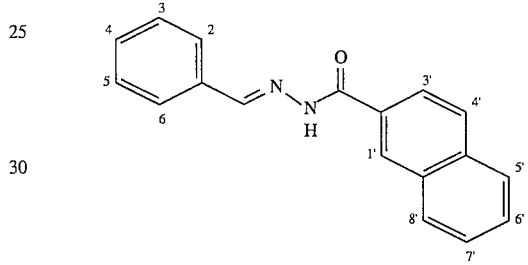

wherein the substitution pattern is advantageously as indicated in Table 3.

TABLE 3

| Compound | Substituents |
|---|---|
| III107A | 2-OH, 3'-OH |
| III111A | 4-NBu$_2$, 3-OH |
| III113A | 4-(3-dimethylpropoxy), 3'-OH |
| IV7A | 3-OMe, 4-(4-NO$_2$-benzyloxy), 3'-OH |
| IV34A | 3-OH, 4-NO$_2$, 3'-OH |
| IV35A | 2,3,4-OH, 3'-OH |

The following additional examples of inhibitors wherein X has a backbone of four atoms are illustrative of the range of structures which may be employed as ring system A, ring system B and linker X. Of course, analogous ring systems and substitution patterns other than those depicted herein would be immediately recognized by those working in the field as equivalent to the structures illustrated and are thus are also contemplated as within the scope of the present invention.

11
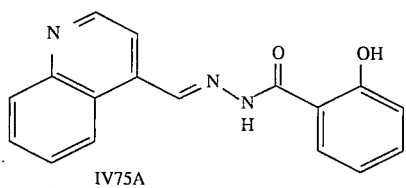
IV75A
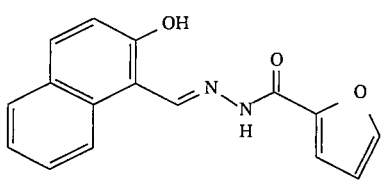
IV48A
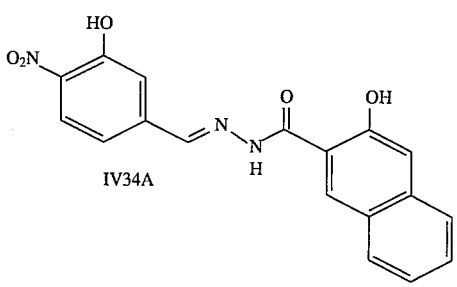
IV34A
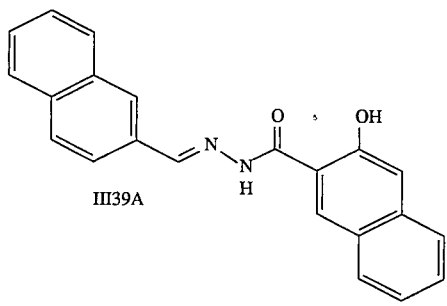
III39A
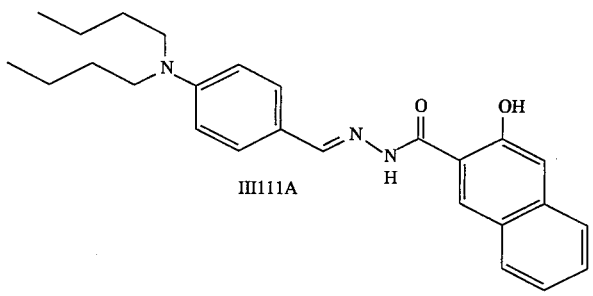
III111A
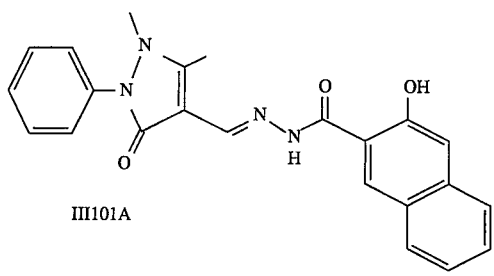
III101A
12
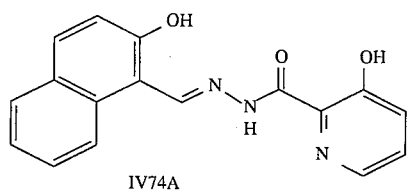
IV74A
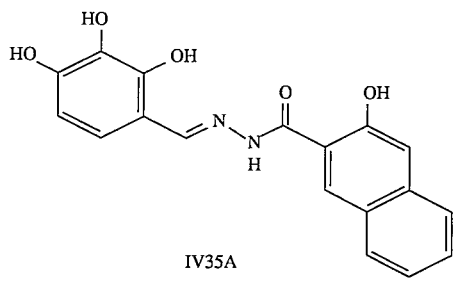
IV35A
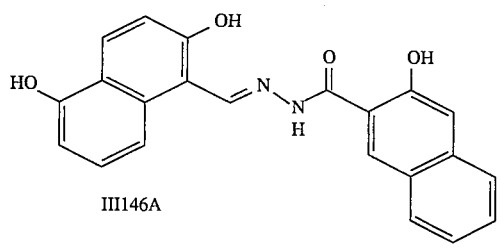
III146A
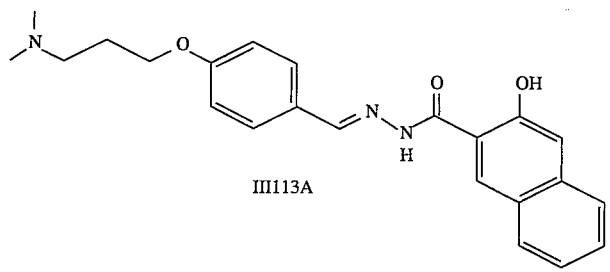
III113A
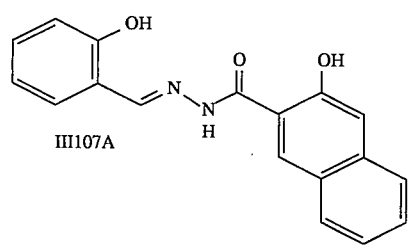
III107A
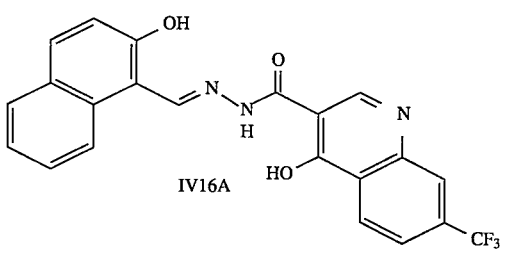
IV16A -continued
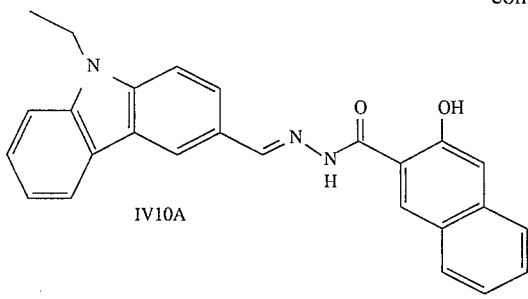
IV10A
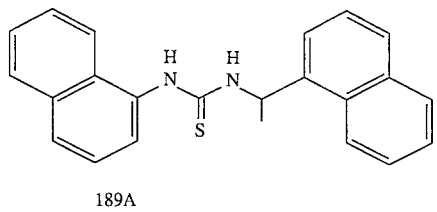
189A
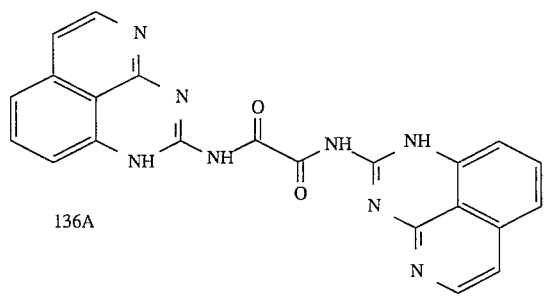
136A
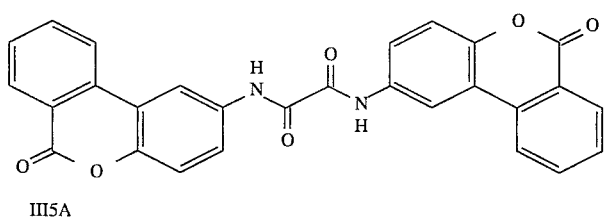
III5A
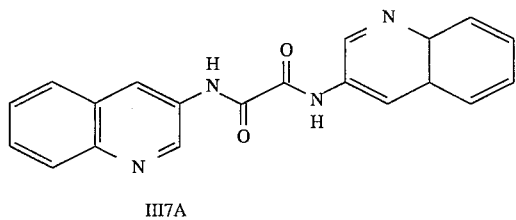
III7A
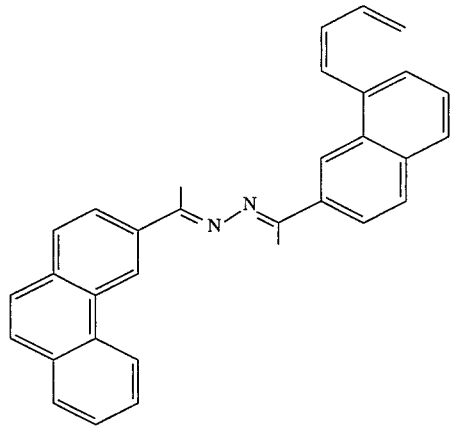
III23A,
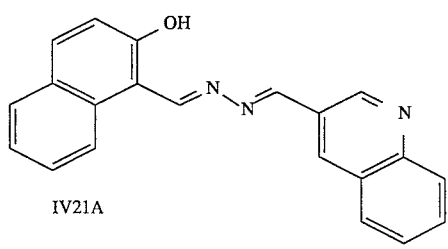
IV21A
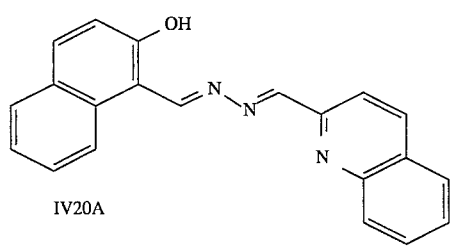
IV20A

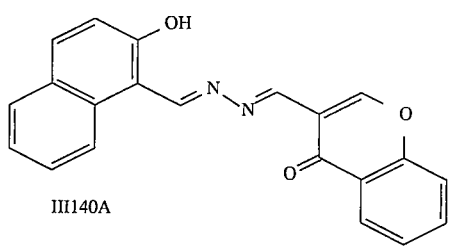

III140A

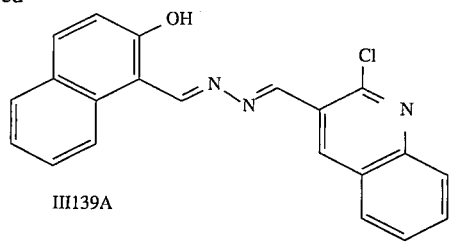

III139A

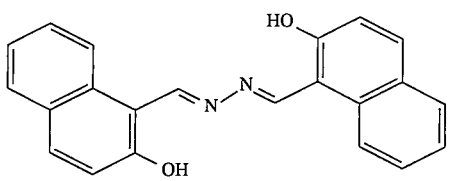

I73A

The following structures are illustrative of inhibitors wherein X has a backbone of 6–8 carbon atoms. Once again, these examples should be viewed as merely illustrative of the range of structures which may be employed as ring system A, ring system B and linker X. Analogous ring systems and substitution patterns other than those depicted herein are contemplated as within the scope of the present invention.

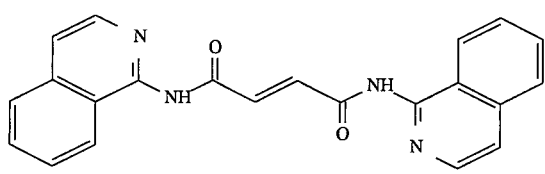

I40A

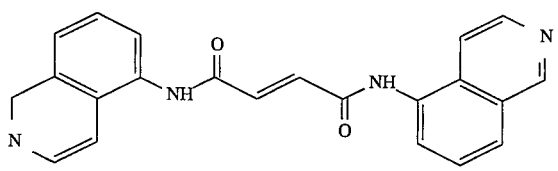

I42A

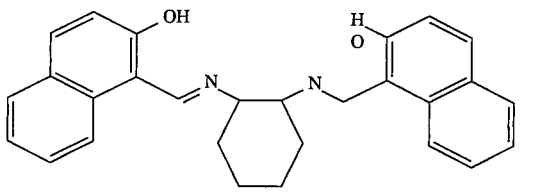

I46A

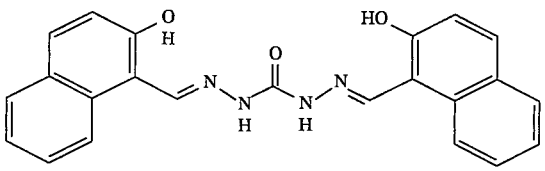

I97A

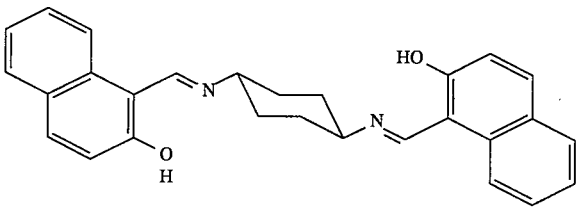

I56A

-continued
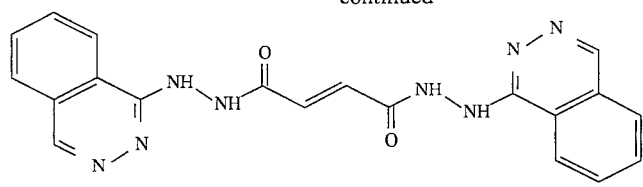
I38A
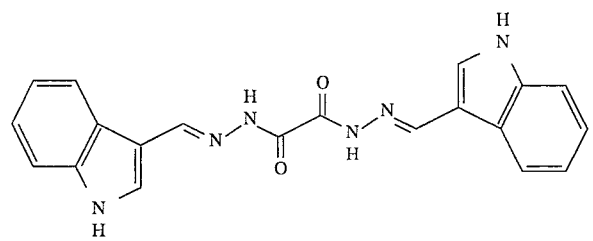
I135A
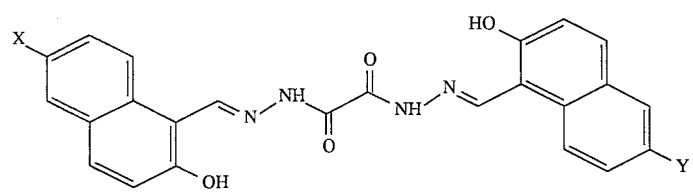
I83A
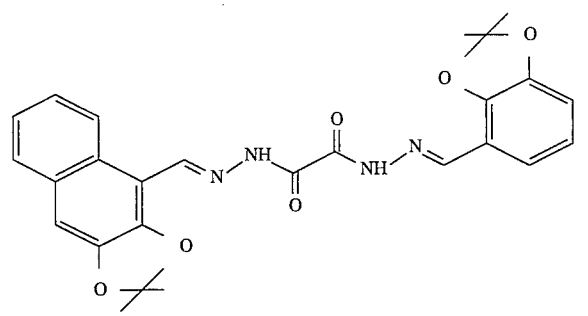
I115A
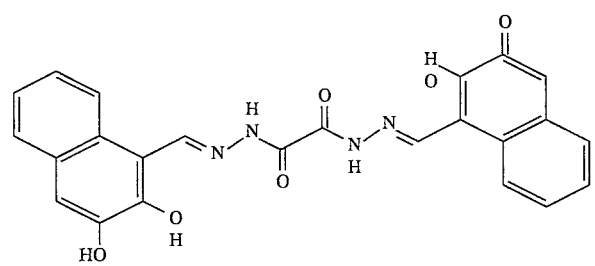
I131A
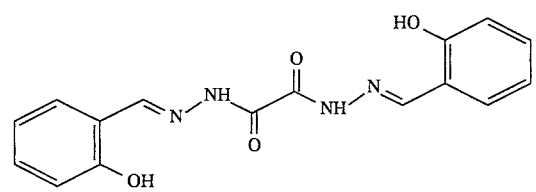
I75A
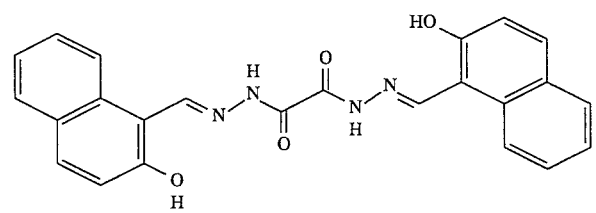
I48A

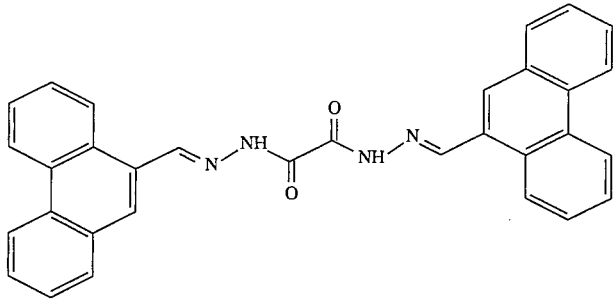

I77A

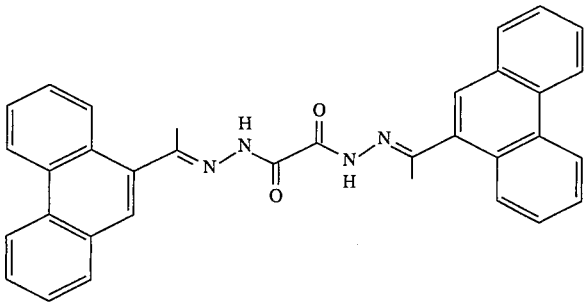

III21A

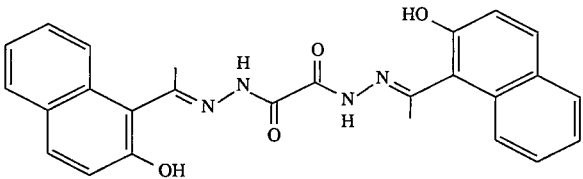

III19A

Finally, the following structures illustrate inhibitors of the general formula

A-X-B'-X'-B'' designed to bond to the S2, S1 and S1' subsites. In these structures, X' is exemplified as follows: a direct ring-to-ring bond; a single-atom backbone linker (e.g., —CH$_2$—); and a two-atom backbone linker (e.g., —CH$_2$—O— and —N=N—). Other X' linkers as hereinbefore specified would be readily apparent substitutes for these exemplary structures. As indicated with respect to the previous structures, these examples should be viewed as merely illustrative of the range of structures which may be employed as ring system A, ring system B and linker X, and once again analogous ring systems and substitution patterns other than those depicted herein are contemplated as within the scope of the present invention.

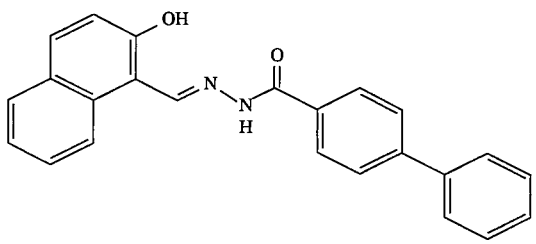

III85A

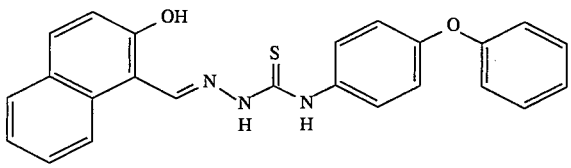

III89A

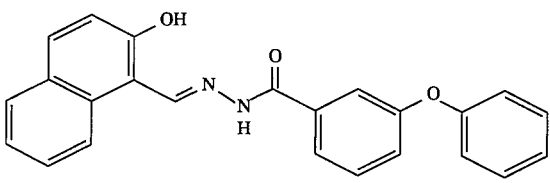

III87A

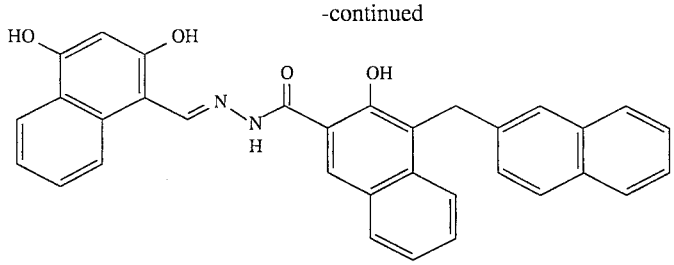

IV56A

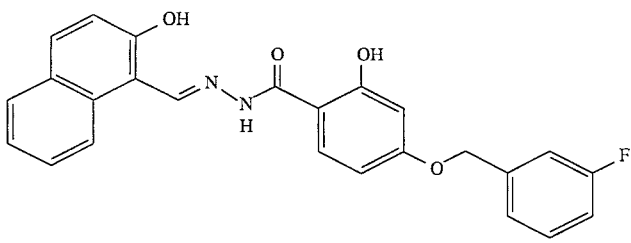

IV82A

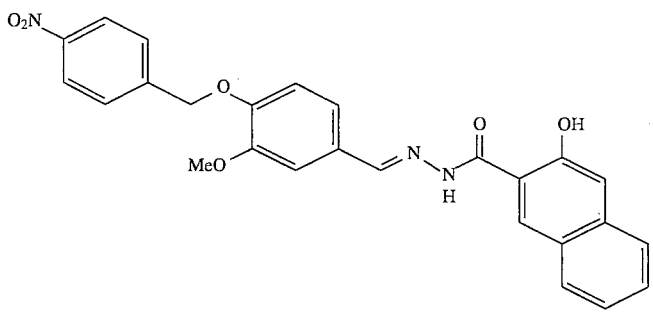

IV7A

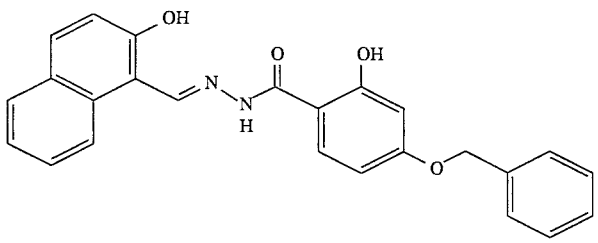

IV61A

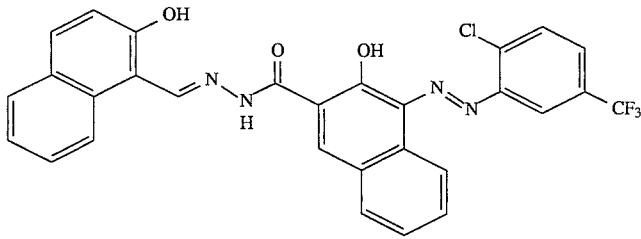

IV17A

Many of the inhibitors employed in accordance with the present invention are either known compounds (some of which are commercially available) or may be readily prepared in a manner known per se from heretofore known and/or commercially-available compounds. The following general schemes illustrate some particularly advantageous synthetic routes; alternative syntheses will of course be readily apparent to those skilled in the field of synthetic organic chemistry.

The synthesis of symmetrical bis-hydrazides and bis-hydrazones within the scope of the present invention (i.e., compounds in which ring system A and ring system B are identical) may readily be effected as follows:

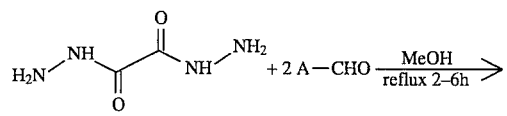

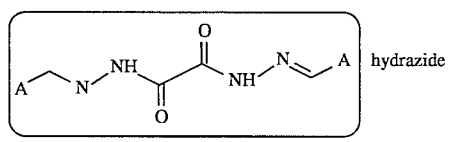 hydrazide

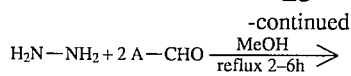
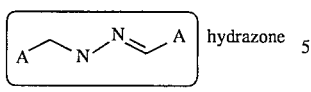

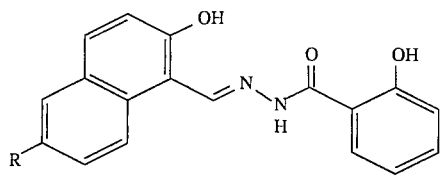

1 R = Br, NO2, NH2

In these illustrations, both ring systems are denominated "A" for clarity. The corresponding aldehydes are either commercially available or may be readily prepared from commercially-available materials by an appropriate reaction scheme (e.g., treatment of the appropriately-substituted precursor with n-butyl lithium and DMF).

The following scheme illustrates a preferred method for synthesis of asymmetrical bis-hydrazides. Although the B ring system is introduced first according to the scheme as illustrated it is of course apparent that the A ring system could equally well be introduced first.

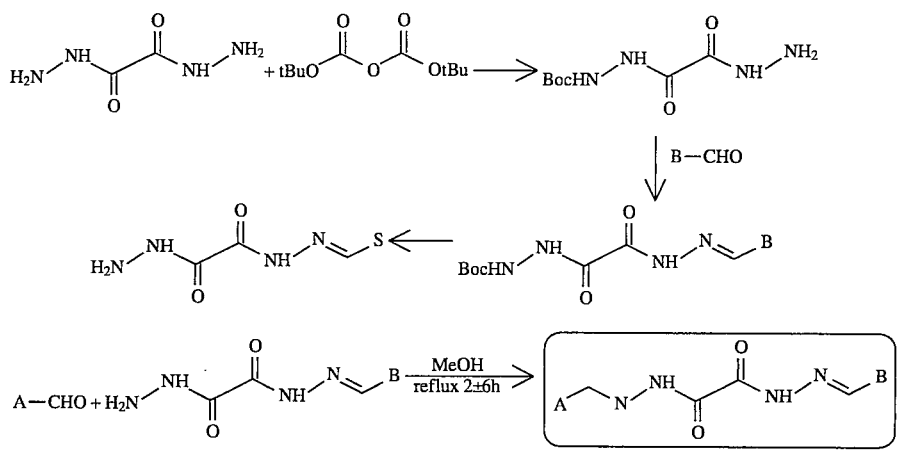

The following scheme illustrates a preferred method for synthesis of asymmetrical bis-hydrazones. Once again, the B ring system is introduced first according to the scheme as illustrated, but it is of course apparent that the A ring system could be the first introduced.

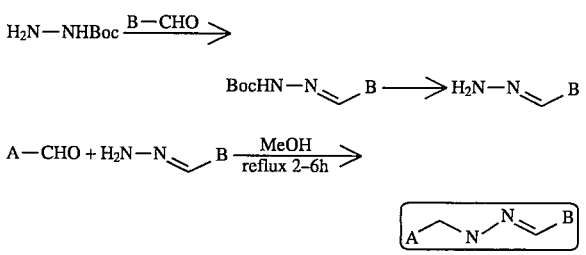

As previously noted, several classes of inhibitors wherein the linker X has a backbone of four atoms in length are of particular interest because they can be synthesized in a one-step condensation of an aldehyde and a hydrazine or hydrazine. The following schemes illustrate such condensations:

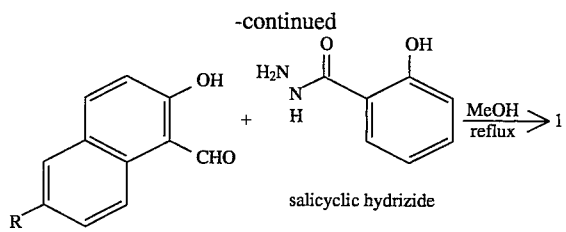

salicyclic hydrizide

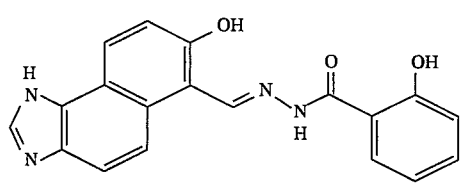

2

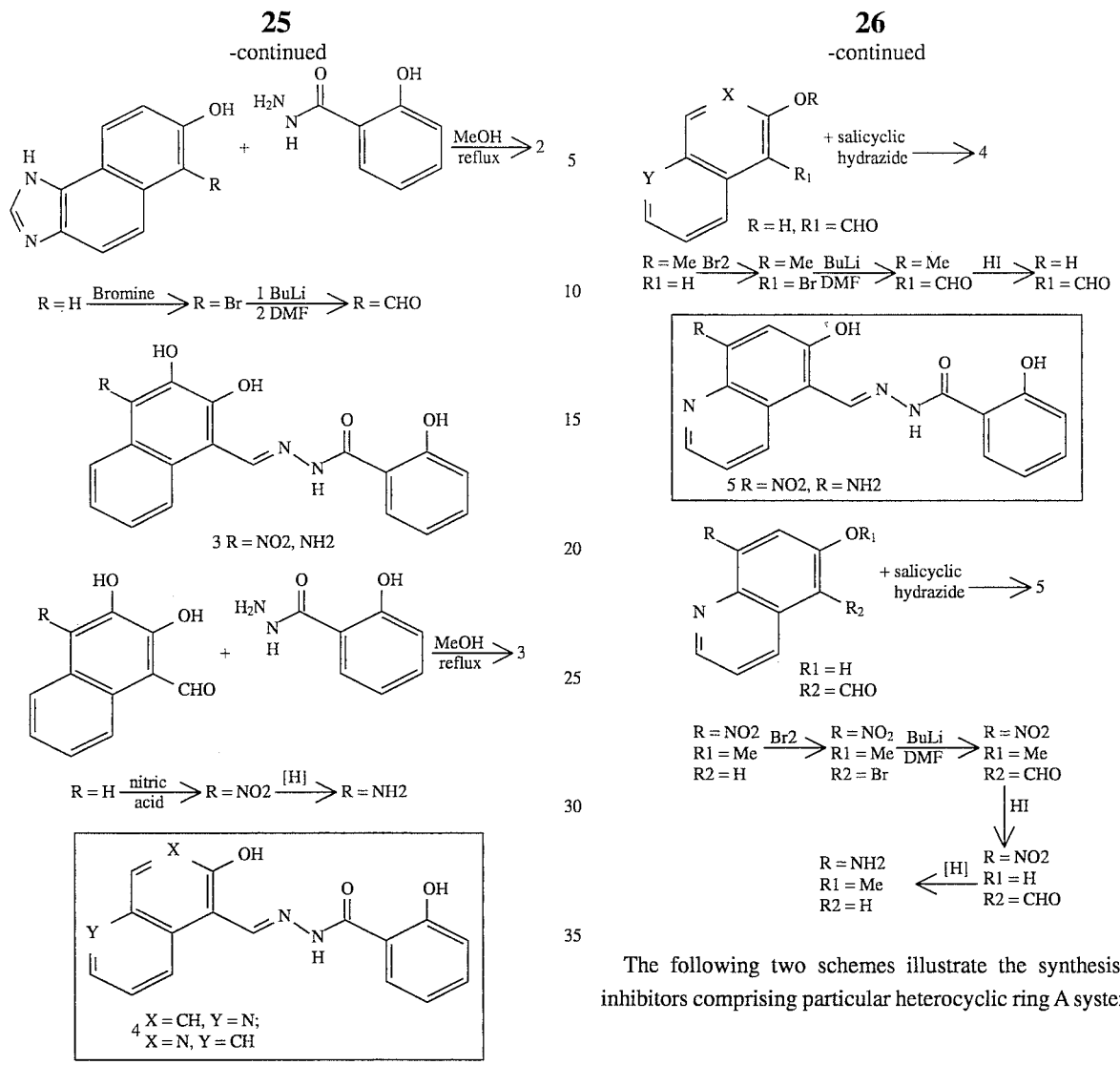
The following two schemes illustrate the synthesis of inhibitors comprising particular heterocyclic ring A systems:

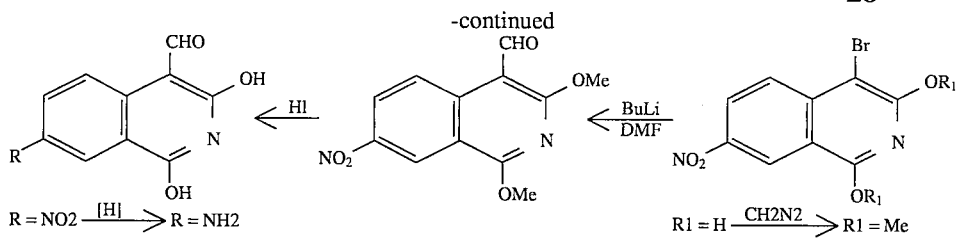
the aldehydes + salicyclic hydrazide ⟶ 6
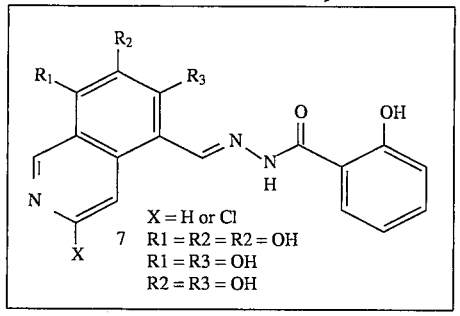
By analogy, a variety of different heterocyclic systems having a desired substitution pattern may be prepared for reaction with the appropriate hydrazide.
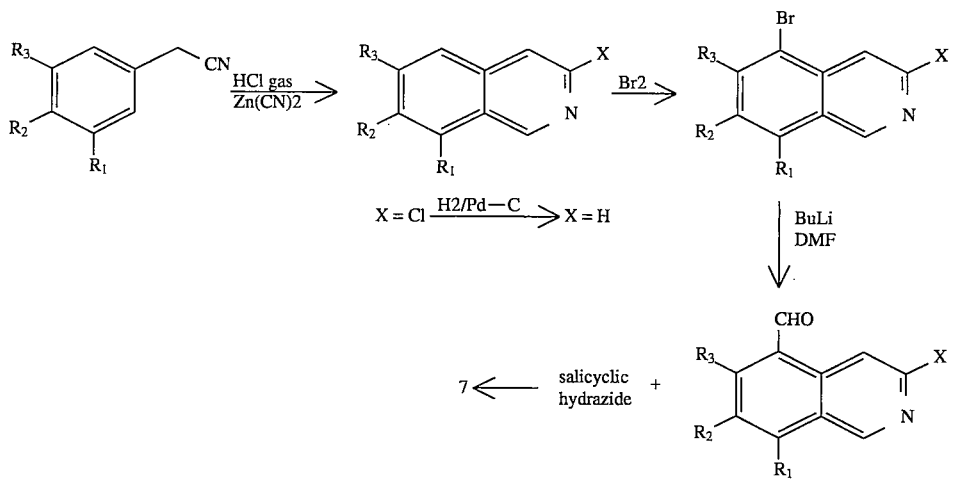
Finally, the following two schemes illustrate a preferred approach for synthesis of inhibitors comprising ring systems A, B' and B":
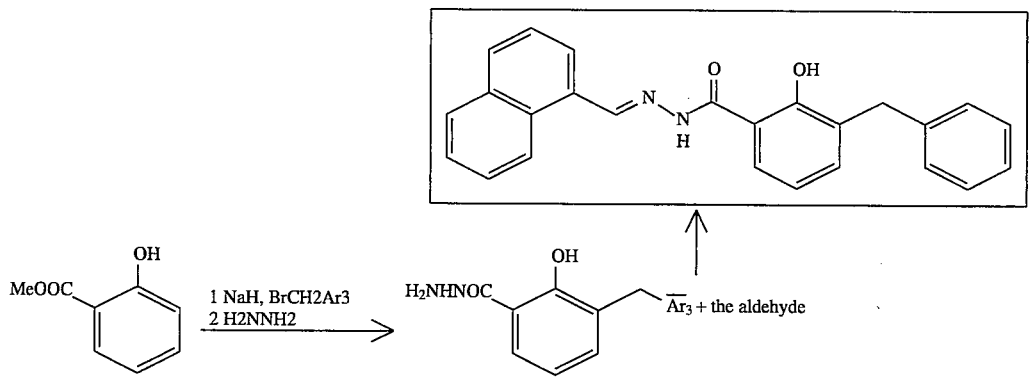

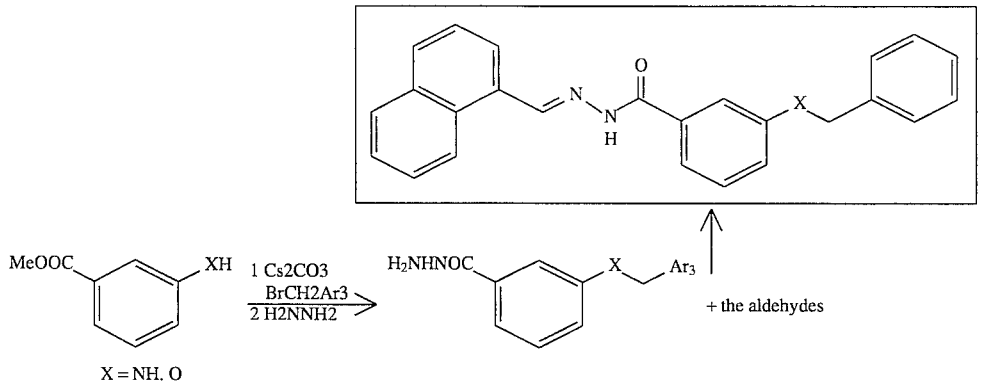

Once again, it would be readily apparent to those skilled in the art that by choice of suitable precursors, other ring systems A, B' and B" may be joined in a similar manner.

The inhibitors employed in the compositions and methods of the present invention are typically administered in conjunction with a suitable carrier or adjuvant. It is presently preferred that the inhibitors be administered in an aqueous solution (e.g., buffered saline); however, other suitable excipients and adjuvants would be readily apparent to those of skill in the art. The compositions of the invention may be administered by a wide variety of known routes of administration (e.g., orally, intravenously, subcutaneously, etc.). The inhibitors are suitably administered at a dosage of about 0.01 to about 10 μM, and preferably about 0.01 to about 1 μM, per kilogram of body weight of the patient per day. Of course, as would be appreciated by those of skill in the art, the optimum dosage for treatment of any given parasitic infection with a composition of the present invention comprising one or more specific inhibitors as described herein may readily be determined empirically.

The inhibitors determined to be effective in accordance with the present invention exhibit a surprising specificity for the malarial protease and other evolutionarily-related metazoan parasite proteases. These metazoan parasite proteases are distinct from proteases found in the parasitic hosts (i.e., mammals), particularly with respect to the chemical environments of the active sites of the respective enzymes. In view of the significant differences between corresponding subsites in the mammalian and the metazoan parasite proteases, the inhibitors of the present invention do not in general inhibit the activity of the host's essential proteases.

For example, the malarial enzyme has an asparagine at position 133, a key residue for determining the specificity of bonding at the S2 subsite; for most other non-parasitic cysteine proteases, however, this residue tends to be either branched hydrophobic or alanine. Specific interactions of the inhibitors in accordance with the present invention with the asparagine increase both specificity and potency. Another modulating residue is glutamic acid at position 205 in the malarial enzyme. The side chain rotamer located at the base of the S2 binding pocket is postulated to change depending upon the nature of the interaction at S2. If the substituent is hydrophobic, the glutamic acid points away from the S2 pocket and presumably interacts with solvent; however, when the substituent is basic, the glutamic acid is thought to point towards the S2 pocket and provide a crucial interaction with the positive charge. Inhibitors that exploit this interaction (i.e., those wherein ring system A has some basic characteristics as a part of the ring system and/or by virtue of the substitution pattern) are thus of particular interest.

The invention may be better understood with reference to the accompanying examples, which are intended for purposes of illustration only and should not be construed as in any sense limiting the scope of the present invention as defined in the claims appended hereto.

EXAMPLES

In the following examples, melting points were determined on a Thomas capillary melting point apparatus and are uncorrected. Proton and carbon NMR spectra were obtained at 300 and 75 MHz, respectively, in DMSO-$d^6$ on a GE QE-300 instrument. Mass spectra (MS) were recorded on a VG-70 mass spectrometer equipped with a Hewlett-Packard 5890A GC. All aldehydes and hydrazides were obtained commercially except for the dihydroxynaphthaldehydes, which were prepared from the corresponding commercially-available dihydroxynaphthalenes according to the literature procedure [Morgan, G. T. & Vining, D. C., J. Chem. Soc 119, 177 (1921)]. 2-Hydroxy-1-naphthaldehyde was recrystallized from EtOH/$H_2O$ (8:2, v/v).

Example 1

Synthesis of 2-hydroxy-1-naphthaldehyde azine (I73A)

In the general procedure for condensation of aldehyde with hydrazine, to a solution of the aldehyde (1 mmol) in methanol (20 mL) was added the corresponding hydrazine or acyl hydrazine (1 mmol) in one portion. The resulting mixture was heated to 65° C. for 3 hours. In most cases, a precipitate was observed after 10 minutes. The precipitate was filtered, washed with hot methanol (50 mL), and dried in vacuum (2 mmHg). If needed, additional purification was performed by recrystallization using appropriate solvents. Following this general procedure, condensation of 2-hydroxy-1-naphthaldehyde and hydrazine gave 2-hydroxy-1-naphthaldehyde azine as a yellow solid (98%): mp>300° C. (dec); $^1$H NMR d 12.90 (br s, 2 H), 9.99 (s, 2 H), 8.64 (d, 2 H, J=8.7 Hz), 8.03 (d, 2 H, J=9.0 Hz), 7.92 (d, 2 H, J=7.8 Hz), 7.61 (t, 2 H, J=7.6 Hz), 7.44 (t, 2 H, J=7.4 Hz), 7.28 (d, 2 H, J =8.7 Hz); HRMS Calcd for $C_{22}H_{16}N_2O_2$:340.1212, found 340.1195; Anal. ($C_{22}H_{16}N_2O_2$) C, H, N.

Example 2

Synthesis of Oxalic bis(2-hydroxy-1-phenylmethylene) hydrazide (I75A)

Following the general procedure of Example 1, condensation of salicylic aldehyde and oxalic dihydrazide gave a white solid (97%): mp>300° C.; $^1$H NMR d 12.65 (s, 2 H), 11.00 (s, 2 H), 8.79 (s, 2H), 7.54 (d, 2 H, J=7.5 Hz), 7.32 (t, 2 H, J=7.6 Hz), 6.91 (m, 4 H); $^{13}$C NMR d 157.58, 155.83, 151.07, 131.99, 129.36, 119.44. 118.59, 116.45; HRMS Calcd for $C_{16}H_{14}N_4O_4$:326.1015, found 326.0997; Anal. ($C_{16}H_{14}N_4O_4$) C, H, N.

Example 3

Synthesis of oxalic bis(9-phenanthrylmethylene) hydrazide (I77A)

Following the general procedure of Example 1, condensation of phenanthrene-9-carboxaldehyde and oxalic dihydrazide gave a white solid (97%): mp>300° C.; MS (CI) m/e 495.4 (M+H)+; Anal. ($C_{32}H_{22}N_4O_2$) C, H, N.

Example 4

Synthesis of 3-hydroxy-2-naphthoic (2-hydroxy-1-naphthylmethylene) hydrazide (I93A)

Following the general procedure of Example 1, condensation of 2-Hydroxy-1-naphthaldehyde and 3-hydroxy-2-naphthoic hydrazide gave a white solid (97%): mp >300° C.; $^1$H NMR d 12.70 (s, 1 H), 12.25 (br s, 1 H), 11.37 (br s, 1 H); 9.58 (s, 1 H), 8.52 (s, 1 H), 8.33 (d, 1 H, J=8.7 Hz), 7.94 (d, 2 H, J=8.7 Hz), 7.89 (d, 1 H, J=8.1 Hz), 7.78 (d, 1 H, J=8.4 Hz), 7.58 (t, 1 H, J=7.6 Hz), 7.52 (t, 1 H, J=7.5 Hz), 7.41 (m, 2 H), 7.37 (s, 1 H), 7.25 (d, 1 H, J=9.0 Hz); $^{13}$C NMR d 163.05, 158.12, 153.88, 147.57, 135.94, 132.90, 131.68, 130.62, 128.90, 128.68, 128.33, 127.79, 127.73, 126.81, 125.85, 123.86, 123.54, 120.98, 119.84, 118.87, 110.62, 108.61; HRMS Calcd for $C_{22}H_{16}N_2O_3$:356.1161, found 356.1151; Anal. ($C_{22}H_{16}N_2O_3$) C, H, N.

Example 5

Synthesis of Bis(2-hydroxy-1-naphthylmethylene) carbohydrazide (I97A)

Following the general procedure of Example 1, condensation of 2-hydroxy-1-naphthaldehyde and carbohydrazide gave a white solid (97%): mp>285° C. (dec); $^1$H NMR d 11.90 (br s, 2 H); 11.05 (s, 2 H), 9.23 (s, 2 H), 8.33 (d, 2 H, J=8.4 Hz), 7.88 (d, 2 H, J=9.0 Hz), 7.87 (d, 2 H, J=7.8 Hz), 7.59 (t, 2 H, J=7.6 Hz), 7.38 (t, 2 H, J=7.5 Hz), 7.22 (d, 2 H, J=9.0 Hz); $^{13}$C NMR d 156.71, 151.56, 143.24, 131.88, 131.50, 128.72, 127.87, 127.56, 123.35, 121.58, 118.61, 109.40; MS (CI) m/e 399.0 (M +H)+; Anal. ($C_{23}H_{18}N_4O_3$0.3 $H_2O$) C, H, N.

Example. 6

Synthesis of Oxalic bis(3-indolylmethylene) hydrazide (I135A)

Following the general procedure of Example 1, condensation of indole-3-carboxaldehyde and oxalic dihydrazide gave a white solid (97%): mp>285° C. (dec); $^1$H NMR d 11.93 (br s, 2 H), 11.66 (s, 2 H), 8.77 (s, 2 H), 8.28 (d, 2 H, J=7.5 Hz), 7.84 (d, 2 H, J=2.1 Hz), 7.46 (d, 2 H, J=7.8 Hz), 7.16 (m, 4 H); $^{13}$C NMR d 156.01, 147.85, 137.09, 131.13, 124.37, 122.77, 121.93, 120.63, 111.95, 111.48; HRMS Calcd for $C_{20}H_{16}N_6O_2$:372.1341, found 372.1335; Anal. ($C_{20}H_{16}N_6O_2$0.3 $H_2O$) C, H, N.

Example 7

Synthesis of 3-Hydroxy-2-naphthoic (2,3-dihydroxy-1-naphthylmethylene) hydrazide (III41A)

Following the general procedure of Example 1, condensation of 2, 3-dihydroxy-1-naphthaldehyde and 3-hydroxy-2-naphthoic hydrazide yielded a yellow crystal (18%) [recrystallized from dioxane/$H_2O$ (1:1, v/v)]: mp>285° C.; $^1$H NMR d 13.16 (br s, 1 H), 12.27 (br s, 1 H), 11.30 (br s, 1 H), 9.74 (br s, 1 H), 9.57 (s, 1 H), 8.53 (s, 1 H), 8.17 (d, 1 H, J=8.2 Hz), 7.95 (d, 1 H, J=8.2 Hz), 7.79 (d, 1 H, J=8.0 Hz), 7.70 (d, 1 H, J=7.7 Hz), 7.54 (t, 1 H, J=7.4 Hz), 7.42–7.25 (m, 5 H); HRMS Calcd for $C_{22}H_{16}N_2O_4$:372.1110, found 372.1103; Anal. ($C_{22}H_{16}N_2O_4$ $H_2O$) C, H, N.

Example 8

Synthesis of 3-Hydroxy-2-naphthoic (2.4-dihydroxy-1-naphthylmethylene) hydrazide (III43A)

Following the general procedure of Example 1, condensation of 2, 4-dihydroxy-1-naphthaldehyde and 3-hydroxy-2-naphthoic hydrazide yielded a yellow crystal (83%) [recrystallized from DMSO/$H_2O$ (8:2, v/v)]: mp>280° C. (dec); $^1$H NMR d 12.42 (br s, 1 H), 11.65 (s, 1 H), 10.96 (br s, 1 H), 10.59 (s, 1 H), 8.99 (s, 1H), 8.07 (s, 1H), 7.77 (d, 1 H, J=8.4 Hz), 7.67 (d, 1 H, J=8.4 Hz), 7.48 (d, 1 H, J=8.1 Hz), 7.32 (d, 1H, J=8.4 Hz), 7.13 (t, 1H, J=7.5 Hz), 7.06 (t, 1 H, J=7.5 Hz), 6.91 (s, 1 H), 6.90 (m, 2 H); $^{13}$C NMR d 162.92, 160.47. 157.70, 154.20, 148.22, 135.97, 132.99, 130.33, 128.72, 128.33 (2 C), 126.84, 125.92, 123.91, 122.94, 122.55, 120.80, 120.32, 119.66, 110.70, 101.38, 100.49; HRMS Calcd for $C_{22}H_{16}N_2O_4$:372.1110, found 372.1095; Anal. ($C_{22}H_{16}N_2O_4$2DMSO $H_2O$) C, H, N.

Example 9

Synthesis of 3-Hydroxy-2-naphthoic (2, 7-dihydroxy-1-naphthylmethylene) hydrazide (III45A)

Following the general procedure of Example 1, condensation of 2, 7-dihydroxy-1-naphthaldehyde and 3-hydroxy-2-naphthoic hydrazide yielded yellow crystals (83%) [recrystallized from DMSO/$H_2O$ (8:2, v/v)]: mp225° C. (dec); $^1$H NMR d 12.75 (s, 1 H), 12.24 (s, 1 H), 11.27 (s, 1 H), 9.93 (s, 1 H), 9.40 (s, 1H), 8.50 (s, 1 H), 7.95 (d, 1 H, J=8.1 Hz), 7.80 (d, 2 H, J=8.7 Hz), 7.73 (d, 1 H, J=8.7 Hz), 7.54 (t, 1 H, J=7.5 Hz), 7.39 (t, 1 H, J=7.5 Hz), 7.37 (s, 1 H), 6.98 (d, 2 H, J=8.7 Hz); HRMS Calcd for $C_{22}H_{16}N_2O_4$:372.1110, found 372.1099; Anal. ($C_{22}H_{16}N_2O_4$1.4 DMSO) C, H, N.

Example 10

Synthesis of 3-Hydroxy-2-naphthoic (2, 6-dihydroxy-1-naphthylmethylene) hydrazide (III79A)

Following the general procedure of Example 1, condensation of 2, 6-dihydroxy-1-naphthaldehyde and 3-hydroxy-2-naphthoic hydrazide yielded a yellow solid (72%): mp>280° C.; $^1$H NMR d 11.89 (s, 1 H), 11.75 (br s, 1 H), 10.90 (br s, 1 H), 9.14 (s, 1 H), 9.03 (s, 1 H), 8.06 (s, 1 H), 7.75 (d, 1 H, J=9.0 Hz), 7.48 (d, 1 H, J=8.4 Hz), 7.33 (d, 1 H, J=8.4 Hz), 7.28 (d, 1 H, J=9.0 Hz), 7.07 (t, 1 H, J=7.6 Hz), 6.92 (t, 1 H, J=7.4 Hz), 6.75–6.67 (m, 3 H), 6.90 (m, 2 H); $^{13}$C NMR d 163.06, 155.90, 153.93, 153.44, 147.82, 135.94, 131.34, 130.57, 129.35, 128.69, 128.34, 126.81, 125.87, 125.66, 123.88, 122.58, 119.86, 119.68, 119.04, 110.62, 110.45, 108.82; HRMS Calcd for $C_{22}H_{16}N_2O_4$:372.1110, found 372.1095; Anal. ($C_{22}H_{16}N_2O_4$0.4 $H_2O$) C, H, N.

Example 11

Synthesis of 3-Hydroxy-2-naphthoic (1-naphthylmethylene) hydrazide (III93A)

Following the general procedure of Example 1, condensation of 1naphthaldehyde and 3-hydroxy-2-naphthoic hydrazide gave a pale yellow solid (76%): mp 214° C.; $^1$H NMR d 11.73 (br s, 1 H), 11.05 (br s, 1 H), 8.72 (s, 1 H), 8.52 (d, 1 H, J=8.4 Hz), 8.13 (s, 1 H), 7.60–6.80 (m, 11 H); $^{13}$C NMR d 164.00, 154.31, 148.56, 135.99, 133.57, 130.80, 130.40. 130.30, 129.48, 128.81, 128.78, 128.29, 128.12, 127.37, 126.85, 126.31. 125.89, 125.54, 124.39, 123.84, 120.13, 110.75; HRMS Calcd for $C_{22}H_{16}N_2O_2$:340.1212, found 340.1208; Anal. ($C_{22}H_{16}N_2O_2$) C, H, N.

Example 12

Synthesis of 3-Hydroxy-2-naphthoic (2-Hydroxy-1phenylmethylene) hydrazide (III107A)

Following the general procedure of Example 1, condensation of salicylic aldehyde and 3-hydroxy-2-naphthoic hydrazide gave a pale yellow solid (94%): mp >285° C.; $^1$H NMR d 11.69 (br s, 1H), 10.97 (br s, 1 H), 10.79 (s, 1 H), 8.24 (s, 1 H), 8.02 (s, 1 H), 7.45 (d, 1 H, J=8.1 Hz), 7.31 (d, 1 H, J=8.1 Hz), 7.12 (dd, 1 H, J=7.8, 0.9 Hz), 7.05 (t, 1 H, J=7.5 Hz), 6.89 (s, 1 H), 6.86 (m, 2H), 6.51 (d, 1 H, J=8.1 Hz), 6.48 (t, 1H, J=7.5 Hz); $^{13}$C NMR d 163.62, 157.54, 154.08, 148.83, 135.94, 131.64, 130.37, 129.49, 128.70, 128.33, 126.79, 125.89, 123.86, 119.99, 119.44, 118.68, 116.48, 110.63; HRMS Calcd for $C_{18}H_{14}N_2O_3$:306.1004, found 306.0977; Anal. ($C_{18}H_{14}N_2O_3$) C, H, N.

Example 13

Synthesis of Salicylic (2-hydroxy-1-naphthylmethylene) hydrazide (III109A)

Following the general procedure of Example 1, condensation of 2-hydroxy-1-naphthaldehyde and salicylic hydrazide yielded a pale yellow solid (74%): mp 265° C.; $^1$H NMR d 12.32 (s, 1 H), 11.65 (br s, 1 H), 11.36 (br s, 1 H), 9.09 (s, 1 H), 7.84 (d, 1 H, J=7.5 Hz), 7.43 (m, 3 H), 7.13 (t, 1 H, J=6.0 Hz), 7.01 (t, 1 H, J=6.6 Hz), 6.83 (t, 1H, J=6.9 Hz), 6.77 (d, 1H, J=8.4 Hz), 6.57 (m, 2 H); $^{13}$C NMR d 163.72, 158.58, 157.88, 147.40, 133.75, 132.63, 131.42, 128.64, 128.49, 127.53, 127.44, 123.27, 120.65, 118.87, 118.61, 117.04, 115.35, 108.32; HRMS Calcd for $C_{18}H_{14}N_2O_3$:306.1004, found 306.0985; Anal. ($C_{18}H_{14}N_2O_3$) C, H, N.

Analytical Data

| entry | | elemental analysis | | |
|---|---|---|---|---|
| | | C % | H % | N % |
| I73A | calcd | 77.63 | 4.74 | 8.23 |
| $C_{22}H_{16}N_2O_2$ | found | 77.71 | 4.90 | 7.93 |
| I75A | calcd | 58.89 | 4.32 | 17.17 |
| $C_{16}H_{14}N_4O_4$ | found | 58.79 | 4.59 | 16.93 |
| I77A | calcd | 77.16 | 4.53 | 11.25 |
| $C_{32}H_{22}N_4O_2 \cdot 0.3H_2O$ | found | 76.94 | 4.13 | 11.53 |
| I93A | calcd | 74.15 | 4.53 | 7.86 |
| $C_{22}H_{16}N_2O_3$ | found | 73.80 | 4.73 | 7.78 |
| I97A | calcd | 68.41 | 4.64 | 13.74 |
| $C_{20}H_{16}N_6O_2 \cdot 0.3H_2O$ | found | 68.33 | 4.59 | 13.97 |
| I135A | calcd | 63.58 | 4.43 | 22.24 |
| $C_{22}H_{16}N_2O_4 \cdot H_2O$ | found | 63.58 | 4.48 | 22.13 |
| III41A | calcd | 67.69 | 4.65 | 7.18 |
| $C_{22}H_{16}N_2O_4 \cdot 2DMSO \cdot H_2O$ | found | 68.09 | 4.35 | 7.13 |
| III43A | calcd | 57.13 | 5.53 | 5.12 |
| $C_{22}H_{16}N_2O_4 \cdot 4DMSO$ | found | 57.45 | 5.33 | 5.11 |
| III45A | calcd | 61.83 | 5.10 | 5.81 |
| $C_{22}H_{16}N_2O_4 \cdot 0.4H_2O$ | found | 61.65 | 4.69 | 5.82 |
| III79A | calcd | 69.61 | 4.46 | 7.38 |
| $C_{22}H_{16}N_2O_4$ | found | 69.64 | 4.81 | 7.33 |
| III93A | calcd | 77.63 | 4.74 | 8.23 |
| $C_{18}H_{14}N_2O_3$ | found | 77.29 | 4.88 | 8.27 |
| III107A | calcd | 70.58 | 4.61 | 9.15 |
| $C_{18}H_{14}N_2O_3$ | found | 70.27 | 4.70 | 9.06 |
| III109A | calcd | 70.58 | 4.61 | 9.15 |
| $C_{16}H_{14}N_2O_3$ | found | 70.59 | 4.69 | 9.04 |

Example 14

Trophozoite cysteine protease inhibitor studies

Enzyme activity was measured with the fluorogenic substrate Z-Phe-Arg-AMC as described in the literature [Rosenthal, P. J. et al., *Mol. Biochem. Parasitol.* 35, 177 (1989)]. Trophozoite extracts were incubated with reaction buffer (in 0.1 M sodium acetate, 10 mM dithiothreitol, pH 5.5) and an appropriate concentration of inhibitor for 30 minutes at room temperature. Z-Phe-Arg-AMC (50 μM final concentration) was then added and fluorescence (380 nM excitation, 460 nM absorbance) was measured continuously over 30 seconds. The slope of fluorescence over time for each inhibitor concentration was compared with that of controls in multiple assays, and the $IC_{50}$ was determined from plots of percent control activity over inhibitor concentration. The results are illustrated in FIG. 1, wherein the points are the mean of 8 assays and the error bars are the standard deviation of the sample. The $IC_{50}$ values for inhibitors in accordance with the present invention are reported in Table 4.

TABLE 4

| COMPOUND | IC50 (μm) |
|---|---|
| I38A | 60 |
| I40A | 18 |
| I42A | >60 |
| I46A | 33 |
| I56A | 50 |
| I73A | 10 |
| I75A | >60 |
| I77A | 10 |
| I83A | 16 |
| I89A | 40 |
| I93A | 10 |
| I97A | 60 |
| I99A | 60 |
| I101A | >60 |
| I115A | 12 |
| III111A | 20 |
| III113A | 40 |
| III115A | 8 |
| III117A | 15 |
| III127A | 20 |
| III128A | 17 |
| III129A | 20 |
| III130A | 14 |
| III132A | 17 |
| III133A | 9 |
| III134A | 20 |
| III135A | 23 |
| III136A | 11 |
| III138A | 15 |
| III139A | 15 |

Example 15

Effect of oxalic his (2-hydroxy-1-naphthylmethylene)hydrazide) on $^3$H-hypoxanthine uptake as a measure parasite metabolism $^3$H-hypoxanthine uptake was measured based on a modification of the method of Desjardins et al. [*Antimicrob. Agents Chemother.* 16, 710–718 (1979)]. Microwell cultures of synchronized ring-stage *P. falciparum* parasites were incubated with inhibitor in DMSO (10% final concentration) for 4 hours. $^3$H-hypoxanthine was added (1μCi/microwell culture) and the cultures were maintained for an additional 36 hours. The cells were then harvested and deposited onto glass fiber filters which were washed and dried with ethanol. $^3$H-hypoxanthine uptake was quantitated by scintillation counting. The uptake at each inhibitor concentration was compared with that of controls and the $IC_{50}$ was determined from plots of percent control uptake over inhibitor concentration. The results are illustrated in FIG. 2.

Example 16

Effect of oxalic bis [(2-hydroxy-1-naphthylmethylene)hydrazide]on ability of parasites to invade red blood cells The FCR3 strain of *Plasmodium falciparum* was maintained in Type O+human erythrocytes (American Red Cross) at 4% hematocrit in RPMI 1640 medium (Gibso supplemented with 10% human serum, hypoxanthine, and gentamicin). Asynchronous infected cells were centrifuged at 500 g for 5 minutes and the supernatant aspirated. Sorbitol (5% in dH20) was added dropwise to the pellet and allowed to incubate for 7 minutes at room temperature. The mixture was centrifuged again and the pellet of synchronous rings were resuspended in the RPMI medium. Medium was changed 12 hours afterward. Potential inhibitors were dissolved in DMSO at the appropriate concentrations. One μl of sample (inhibitor) and 49 μl of RPMI medium without human serum (incomplete medium) were plated per well in 96 well plates. For the negative control, one μl of DMSO and 49 μl of incomplete medium was used. For the positive control, 50 μl of Heparin at 10 μg/ml in incomplete medium was used. At 24–27 hours after sorbitol treatment, synchronous parasites in the trophozoite stage were cultured at 3.0%–4.5% parasitemia at 3% hematocrit and 150 μl of this culture was aliquoted to each well. Plates were incubated for 26–28 hours at 40 degrees Centigrade to allow the parasites to develop schizonts, segment into merozoites and attempt invasion. After incubation, the supernatant above the settled cells was removed. For each well, about 2 μl of the cells was used for a smear and about 3 μl for flow-cytometry measurement of parasitemia.

Figure 4:
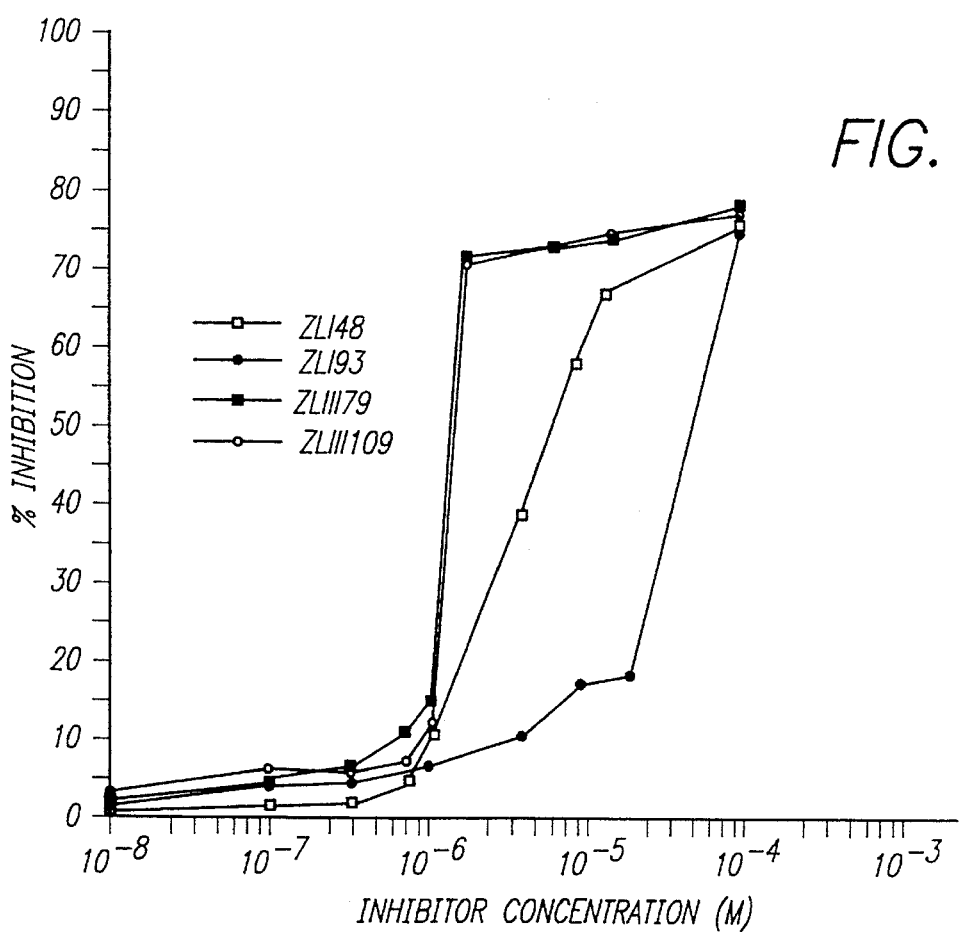
FIG. 4 illustrates inhibition of the parasite's ability to invade red blood cells by oxalic bis-[(2-hydroxyl-1-naphthylmethylene)hydrazide].

For each well, about 3 μl cells were fixed via incubation in a culture tube containing 2 ml of 0.01% glutaraldehyde for at least one hour at room temperature. Tubes were centrifuged at 250 g for 5 minutes, supernatant aspirated and cells resuspended in Dulbeco's PBS to rime off the glutaraldehyde. Tubes were centrifuged again, PBS aspirated and cells resuspended in 0.05 mg/ml propidium iodide to cause fluorescence of parasite DNA. Tubes were shielded from light and incubated in the propidium iodide overnight at room temperature. For each sample, 20,000 cells were analyzed on the FACS flow cytometer and the parasitemia determined based on the greater intensity of fluorescence of infected cells. Percent inhibition as reported in FIG. 4 is the ratio of sample parasitemia to negative control substrated from 100%. The $IC_{50}$ values as determined in this assay for specific inhibitors in accordance with the present invention are reported in Table 5.

TABLE 5

$IC_{50}$ of Inhibitors

| Compound | Malaria Whole Parasite Red Blood Cell Infectivity Assay |
|---|---|
| 148A | 6 μM |
| III43A | 1.7 μM |
| III79A | 1.3 μM |
| III109A | 0.5 μM |
| I93A | 5.8 μM |
| III128A | 6.2 μM |
| III129A | 4.0 μM |
| III41A | 5.0 μM |
| III45A | 5.2 μM |
| III103A | 6.5 μM |
| 87A | 3.1 μM |
| III111A | 3.8 μM |

Example 17

Inhibition of critical cysteine proteases from other parasites

Stock solutions (25 μM) of the protease substrate, N-CBZ-Phe-Arg-7-AMC, and 10 mM of inhibitors were prepared in DMSO. A stock solution (1M) dithiothreitol was prepared in 10 mM sodium acetate, pH 6. Protease assays contained per reaction a constant amount of: 27 μg purified protease, 3.3 mM DDT, and 33 μM protease substrate. The concentration range of protease inhibitors used was 10 nM to 100 μM. Sodium acetate buffer (100 mM, pH 5.5) was added to a final volume of 1.5 ml per reaction. The variation in the absorbance was measured at 460 nm in a spectrofluorometer. The results are reported in Table 6.

TABLE 6

$IC_{50}$ of Inhibitors Against Other Parasite Cysteine Proteases and Human Cathepsin B

| Compound | T. cruzi Cruzain | S. mansoni Hemoglobinase | Human Cathepsin B |
|---|---|---|---|
| 148A | 13 μM | No inhib. | No inhib. |
| III43A | 9.0 μM | 9.3 μM | No inhib. |
| III79A | 24 μM | 7.6 μM | No inhib. |
| III109A | 21 μM | 2.9 μM | No inhib. |

What is claimed is:

1. A method for treating a patient infected with a metazoan parasite, said method comprising administering an amount effective to kill the parasite of at least one metazoan protease inhibitor of general formula

A-X-B wherein A is a substituted or unsubstituted homoaromatic ring system comprising one to three rings which binds to the S2 subsite of the metazoan protease;

B is a substituted or unsubstituted homoaromatic ring system comprising one to three rings which binds to the S1 or S1' subsite of the metazoan protease;

X is a linker comprising a substantially planar linear array with a backbone of four to eight atoms in length;

wherein A and B are not heterocycles, and X is selected from the group consisting of:

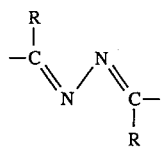

wherein R is hydrogen or lower alkyl;

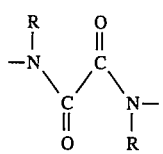

wherein R is hydrogen or lower alkyl;

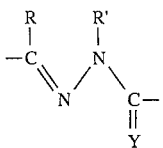

wherein R is hydrogen or lower alkyl, R' is hydrogen, lower alkyl, or aryl, and Y is O or S;

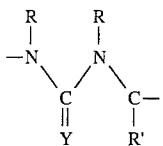

wherein R is hydrogen or lower alkyl, R' is hydrogen, lower alkyl, or aryl, and Y is O or S;

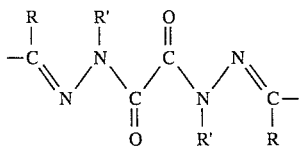

wherein R is hydrogen or lower alkyl and R' is hydrogen, lower alkyl, or aryl;

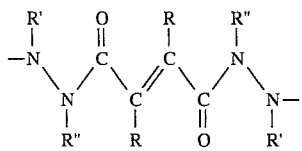

wherein R and R" are independently selected from hydrogen and lower alkyl; and R' is independently selected from hydrogen, lower alkyl, and aryl;

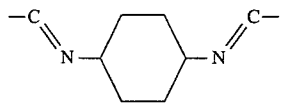

and

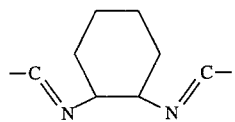

wherein the cyclohexyl group is unsubstituted or substituted; and

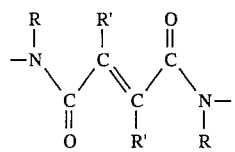

wherein R is independently selected from hydrogen and lower alkyl; and R' is independently selected from hydrogen, lower alkyl, and aryl.

2. A method according to claim 1, wherein the metazoan parasite is selected from the group consisting of *Plasmodium falciparum, Schistosoma mansoni, Trypanosoma cruzi, Giardia lamblia, Entoemeba histolytica*, Cryptospiridium spp., Leishmania spp., Brugia spp., Wuchereria spp., Onchocerca spp., Strongyloides spp., Coccidia, Haemanchus spp., Ostertagia spp., Trichomonas spp., Dirofilaria spp., Toxocara spp., Naegleria spp., *Pneumocystis carinii*, Ascaris spp., other Trypanosoma spp., other Schistosome spp., other Plasmodium spp., Babesia spp., Theileria spp., Anisakis and *Isospora beli*.

3. A method according to claim 1, wherein the metazoan protease inhibitor is administered at a dosage of about 0.01 to about 10 μM per kilogram of body weight of patient per day.

4. A method according to claim 3, wherein the metazoan protease inhibitor is administered at a dosage of about 0.01 to about 1 μM per kilogram of body weight of patient per day.

5. A method according to claim 1, wherein A is selected from the group consisting of phenyl, 1-naphthyl, 1-isoquinolyl, 1-phthalazinyl, 3-coumarinyl, 9-phenanthryl and 1-quinolyl.

6. A method according to claim 1, wherein B is selected from the group consisting of phenyl, 1-naphthyl, 2-naphthyl, 1-isoquinolyl, 1-phthalazinyl, 3-coumarinyl, 9-phenanthryl, 1-quinolyl, 2-quinolyl, 3-quinolyl, 6-coumarinyl and 2-chromonyl.

7. A method according to claim 1, wherein at least one of A, B and X is substituted by at least one substituent selected from the group consisting of hydroxyl, lower alkyl, lower alkoxy, amino, mono-and di-(lower-alkyl)-amino, —NO$_2$, halogen, aryl, aryloxy, —COOH and —COOR', wherein R' is hydrogen, lower alkyl or aryl.

8. A method according to claim 1, wherein A is unsubstituted or substituted 1-naphthyl and B is unsubstituted or substituted 2-naphthyl or phenyl.

9. A method according to claim 1, wherein X is

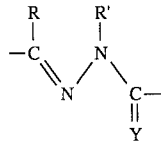

in which R is hydrogen or lower alkyl, R' is hydrogen or lower alkyl and Y is O or S.

10. A composition for treating a patient infected with a metazoan parasite, said composition comprising a suitable carrier or excipient and an amount effective to kill the parasite of at least one metazoan protease inhibitor of general formula

A-X-B wherein A is a substituted or unsubstituted homoaromatic ring system comprising one to three rings which binds to the S2 subsite of the metazoan protease;

B is a substituted or unsubstituted homoaromatic ring system comprising one to three rings which binds to the S1 or S1' subsite of the metazoan protease;

X is a linker comprising a substantially planar linear array with a backbone of four to eight atoms in length;

wherein A and B are not heterocycles, and X is selected from the group consisting of:

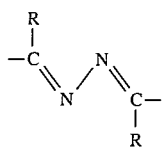

wherein R is hydrogen or lower alkyl;

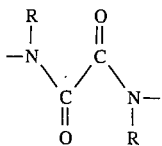

wherein R is hydrogen or lower alkyl;

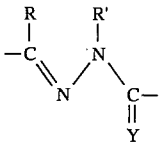

wherein R is hydrogen or lower alkyl, R' is hydrogen, lower alkyl, or aryl, and Y is O or S;

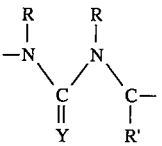

wherein R is hydrogen or lower alkyl, R' is hydrogen, lower alkyl, or aryl, and Y is O or S;

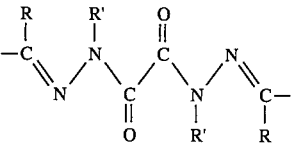

wherein R is hydrogen or lower alkyl and R' is hydrogen, lower alkyl, or aryl;

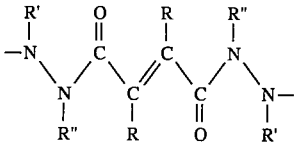

wherein R' and R" are independently selected from hydrogen and lower alkyl; and R' is independently selected from hydrogen, lower alkyl, and aryl;

and

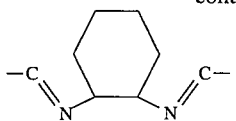

wherein the cyclohexyl group is unsubstituted or substituted; and

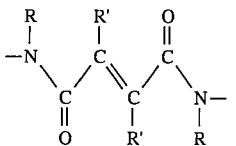

wherein R is independently selected from hydrogen and lower alkyl; and R' is independently selected from hydrogen, lower alkyl, and aryl.

11. A composition according to claim 10, wherein the metazoan parasite is selected from the group consisting of *Plasmodium falciparum, Schistosoma mansoni, Trypanosoma cruzi, Giardia lamblia, Entoemeba histolytica,* Cryptospiridium spp., Leishmania spp., Brugia spp., Wuchereria spp., Onchocerca spp., Strongyloides spp., Coccidia, Haemanchus spp., Ostertagia spp., Trichomonas spp., Dirofilaria spp., Toxocara spp., Naegleria spp., *Pneumocystis carinii,* Ascaris spp., other Trypanosoma spp., other Schistosome spp., other Plasmodium spp., Babesia spp., Theileria spp., Anisakis and *Isospora beli.*

12. A composition according to claim 10, in a dosage unit form wherein the metazoan protease inhibitor is present in an amount sufficient to provide about 0.01 to about 10 μM per kilogram of body weight of patient per day.

13. A composition according to claim 12, in a dosage unit form wherein the metazoan protease inhibitor is present in an amount sufficient to provide about 0.01 to about 1μM per kilogram of body weight of patient per day.

14. A composition according to claim 10, wherein A is selected from the group consisting of phenyl, 1-naphthyl, 1-isoquinolyl, 1-phthalazinyl, 3-coumarinyl, 9-phenanthryl and 1-quinolyl.

15. A composition according to claim 10, wherein B is selected from the group consisting of phenyl, 1-naphthyl, 2-naphthyl, 1-isoquinolyl, 1-phthalazinyl, 3-coumarinyl, 9-phenanthryl, 1-quinolyl, 2-quinolyl, 3-quinolyl, 6-coumarinyl and 2-chromonyl.

16. A composition according to claim 10, wherein at least one of A, B and X is substituted by at least one substituent selected from the group consisting of hydroxyl, lower alkyl, lower alkoxy, amino, mono- and di-(lower-alkyl)-amino, —NO₂, halogen, aryl, aryloxy, —COOH and —COOR', wherein R' is hydrogen, lower alkyl or aryl.

17. A composition according to claim 10, wherein A is unsubstituted or substituted 1-naphthyl and B is unsubstituted or substituted 2-naphthyl or phenyl.

18. A composition according to claim 10, wherein X is

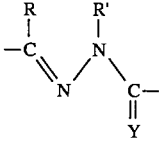

in which R is hydrogen or lower alkyl, R' is hydrogen or lower alkyl and Y is O or S.

* * * * *